US010561353B2

(12) United States Patent
Lucisano et al.

(10) Patent No.: US 10,561,353 B2
(45) Date of Patent: Feb. 18, 2020

(54) BIOCOMPATIBLE IMPLANTABLE SENSOR APPARATUS AND METHODS

(71) Applicant: GlySens Incorporated, San Diego, CA (US)

(72) Inventors: Joseph Lucisano, San Diego, CA (US); Bahman Javidi, Poway, CA (US); Lev Kurbanyan, Granada Hills, CA (US); Joe Lin, San Diego, CA (US); Timothy Routh, San Diego, CA (US); Bradley Walker, San Diego, CA (US)

(73) Assignee: GLYSENS INCORPORATED, San Diego, CA (US)

( * ) Notice: Subject to any disclaimer, the term of this patent is extended or adjusted under 35 U.S.C. 154(b) by 515 days.

(21) Appl. No.: 15/170,571

(22) Filed: Jun. 1, 2016

(65) Prior Publication Data
US 2017/0347932 A1 Dec. 7, 2017

(51) Int. Cl.
*A61B 5/05* (2006.01)
*A61B 5/1486* (2006.01)
(Continued)

(52) U.S. Cl.
CPC ........ *A61B 5/14865* (2013.01); *A61B 5/0031* (2013.01); *A61B 5/076* (2013.01);
(Continued)

(58) Field of Classification Search
CPC ... A61B 5/07; A61B 5/14532; A61B 5/14546; A61B 5/1473; A61B 5/0031; A61B 5/14865
See application file for complete search history.

(56) References Cited

U.S. PATENT DOCUMENTS 2,508,523 A   5/1950  Krebs
2,563,062 A   8/1951  Perley
(Continued)

FOREIGN PATENT DOCUMENTS

CN   1355670 A   6/2002
CN   1592570 A   3/2005
(Continued)

OTHER PUBLICATIONS

Alvarez-Icaza M., et al., "Mass Production of Biosensors," Analytical Chemistry, 1993, vol. 65 (11), pp. 525-533.
(Continued)

*Primary Examiner* — Eric J Messersmith
(74) *Attorney, Agent, or Firm* — Gazdzinski & Associates, PC

(57) ABSTRACT

Enzymatic and non-enzymatic detectors and associated membrane apparatus, and methods of use, such as within a fully implantable sensor apparatus. In one embodiment, detector performance is controlled through selective use of membrane configurations and enzyme region shapes, which enable accurate detection of blood glucose level within the solid tissue of the living host for extended periods of time. Isolation between the host's tissue and the underlying enzymes and reaction byproducts used in the detectors is also advantageously maintained in one embodiment via use of a non-enzyme containing permeable membrane formed of e.g., a biocompatible crosslinked protein-based material. Control of response range and/or rate in some embodiments also permits customization of sensor elements. In one variant, heterogeneous detector elements are used to, e.g., accommodate a wider range of blood glucose concentration within the host. Methods of manufacturing the membranes and detectors, including methods to increase reliability, are also disclosed.

30 Claims, 8 Drawing Sheets

(51) Int. Cl.
  *A61B 5/00* (2006.01)
  *A61B 5/07* (2006.01)
  *A61B 5/145* (2006.01)
  *A61B 5/1473* (2006.01)

(52) U.S. Cl.
  CPC ........ *A61B 5/1473* (2013.01); *A61B 5/14532* (2013.01); *A61B 5/14542* (2013.01); *A61B 5/6861* (2013.01); *A61B 2562/0209* (2013.01); *A61B 2562/04* (2013.01)

(56) References Cited

U.S. PATENT DOCUMENTS

| | | |
|---|---|---|
| 2,805,191 A | 9/1957 | Hersch |
| 2,864,750 A | 12/1958 | Hughes, Jr. et al. |
| 2,998,371 A | 8/1961 | Sabins |
| 3,099,575 A | 7/1963 | Hill |
| 3,246,235 A | 4/1966 | Allsopp |
| 3,249,250 A | 5/1966 | McKee |
| 3,300,345 A | 1/1967 | Lyons, Jr. |
| 3,308,046 A | 3/1967 | Suleski |
| 3,458,421 A | 7/1969 | Harald |
| 3,505,195 A | 4/1970 | Borge et al. |
| 3,542,662 A | 11/1970 | Hicks et al. |
| 3,616,412 A | 10/1971 | Gnage |
| 3,957,613 A | 5/1976 | Macur |
| 4,036,716 A | 7/1977 | Hulthe |
| 4,088,550 A | 5/1978 | Malkin |
| 4,240,438 A | 12/1980 | Shults et al. |
| 4,306,952 A | 12/1981 | Jansen |
| 4,340,457 A | 7/1982 | Kater |
| 4,361,153 A | 11/1982 | Slocum et al. |
| 4,366,033 A | 12/1982 | Richter et al. |
| 4,431,004 A | 2/1984 | Bessman et al. |
| 4,458,686 A | 7/1984 | Clark, Jr. |
| 4,484,987 A | 11/1984 | Gough |
| 4,494,950 A | 1/1985 | Fischell |
| 4,541,431 A | 9/1985 | Ibrahim et al. |
| 4,550,732 A | 11/1985 | Batty, Jr. et al. |
| 4,553,547 A | 11/1985 | Keimel |
| 4,571,589 A | 2/1986 | Slocum et al. |
| 4,637,861 A | 1/1987 | Krull et al. |
| 4,650,547 A | 3/1987 | Gough |
| 4,671,288 A | 6/1987 | Gough |
| 4,703,756 A | 11/1987 | Gough et al. |
| 4,746,218 A | 5/1988 | Lord, III |
| 4,748,562 A | 5/1988 | Miller et al. |
| 4,759,828 A | 7/1988 | Young et al. |
| 4,781,798 A | 11/1988 | Gough |
| 4,830,713 A | 5/1989 | Gagescu |
| 4,890,620 A | 1/1990 | Gough |
| 5,042,902 A | 8/1991 | Huebscher et al. |
| 5,046,242 A | 9/1991 | Kuzma |
| 5,077,476 A | 12/1991 | Rosenthal |
| 5,105,811 A | 4/1992 | Kuzma |
| 5,112,455 A | 5/1992 | Cozzette et al. |
| 5,150,516 A | 9/1992 | Boero et al. |
| 5,165,406 A | 11/1992 | Wong |
| 5,189,717 A | 2/1993 | Larson et al. |
| 5,264,103 A | 11/1993 | Yoshioka et al. |
| 5,272,283 A | 12/1993 | Kuzma |
| 5,273,203 A | 12/1993 | Webster |
| 5,283,104 A | 2/1994 | Aoude et al. |
| 5,283,204 A | 2/1994 | Rhodes et al. |
| 5,284,140 A | 2/1994 | Allen et al. |
| 5,322,063 A | 6/1994 | Allen et al. |
| 5,337,475 A | 8/1994 | Aoude et al. |
| 5,395,504 A | 3/1995 | Asulab |
| 5,431,160 A | 7/1995 | Wilkins |
| 5,487,855 A | 1/1996 | Moeggenborg et al. |
| 5,497,772 A | 3/1996 | Schulman et al. |
| 5,560,098 A | 10/1996 | Robins |
| 5,660,163 A | 8/1997 | Schulman et al. |
| 5,692,299 A | 12/1997 | Daems et al. |
| 5,695,623 A | 12/1997 | Michel et al. |
| 5,711,861 A | 1/1998 | Ward et al. |
| 5,727,283 A | 3/1998 | Webster |
| 5,741,330 A | 4/1998 | Brauker et al. |
| 5,750,926 A | 5/1998 | Schulman et al. |
| 5,776,324 A | 7/1998 | Usala |
| 5,777,060 A | 7/1998 | Van Antwerp |
| 5,782,755 A | 7/1998 | Chance et al. |
| 5,782,891 A | 7/1998 | Hassler et al. |
| 5,791,344 A | 8/1998 | Schulman et al. |
| 5,804,048 A | 9/1998 | Wong et al. |
| 5,821,011 A | 10/1998 | Taylor et al. |
| 5,842,983 A | 12/1998 | Abel et al. |
| 5,855,995 A | 1/1999 | Haq et al. |
| 5,864,088 A | 1/1999 | Sato et al. |
| 5,882,494 A | 3/1999 | Van Antwerp |
| 5,887,240 A | 3/1999 | Fournier et al. |
| 5,932,175 A | 8/1999 | Knute et al. |
| 5,942,842 A | 8/1999 | Fogle, Jr. |
| 5,964,993 A | 10/1999 | Blubaugh, Jr. et al. |
| 5,985,129 A | 11/1999 | Gough et al. |
| 6,001,067 A | 12/1999 | Shults |
| 6,027,479 A | 2/2000 | Alei et al. |
| 6,041,496 A | 3/2000 | Haq et al. |
| 6,081,736 A | 6/2000 | Colvin et al. |
| 6,090,503 A | 7/2000 | Taylor et al. |
| 6,096,066 A | 8/2000 | Chen et al. |
| 6,107,083 A | 8/2000 | Collins et al. |
| 6,119,208 A | 9/2000 | White et al. |
| 6,193,421 B1 | 2/2001 | Tamekuni et al. |
| 6,200,772 B1 | 3/2001 | Vadgama et al. |
| 6,212,416 B1 | 4/2001 | Ward et al. |
| 6,221,513 B1 | 4/2001 | Lasater |
| 6,403,944 B1 | 6/2002 | Mackenzie et al. |
| 6,466,810 B1 | 10/2002 | Ward et al. |
| 6,516,808 B2 | 2/2003 | Schulman |
| 6,551,252 B2 | 4/2003 | Sackner et al. |
| 6,558,321 B1 | 5/2003 | Burd et al. |
| 6,642,015 B2 | 11/2003 | Vachon et al. |
| 6,721,587 B2 | 4/2004 | Gough |
| 6,741,877 B1 | 5/2004 | Shults et al. |
| 6,809,607 B2 | 10/2004 | Nagasaka |
| 6,812,404 B1 | 11/2004 | Martinez |
| 6,832,114 B1 | 12/2004 | Whitehurst et al. |
| 6,843,107 B2 | 1/2005 | Newman et al. |
| 6,931,268 B1 | 8/2005 | Kiani-Azarbayjany et al. |
| 7,005,796 B2 | 2/2006 | Kolluri et al. |
| 7,079,881 B2 | 7/2006 | Schulman et al. |
| 7,106,939 B2 | 9/2006 | Labrake et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,140,787 B2 | 11/2006 | Yamauchi et al. |
| 7,146,203 B2 | 12/2006 | Botvinick et al. |
| 7,161,727 B2 | 1/2007 | Callies et al. |
| 7,189,341 B2 | 3/2007 | Li et al. |
| 7,192,450 B2 | 3/2007 | Brauker et al. |
| 7,226,978 B2 | 6/2007 | Tapsak et al. |
| 7,248,912 B2 | 7/2007 | Gough et al. |
| 7,323,142 B2 | 1/2008 | Pendo et al. |
| 7,336,984 B2 | 2/2008 | Gough et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,988 B2 | 1/2009 | Ok et al. |
| 7,497,827 B2 | 3/2009 | Brister et al. |
| 7,514,791 B2 | 4/2009 | Shah et al. |
| 7,525,298 B2 | 4/2009 | Morgan et al. |
| 7,761,130 B2 | 7/2010 | Simpson et al. |
| 7,857,760 B2 | 12/2010 | Brister et al. |
| 7,871,456 B2 | 1/2011 | Gough et al. |
| 7,875,293 B2 | 1/2011 | Shults et al. |
| 7,881,763 B2 | 2/2011 | Brauker et al. |
| 7,894,870 B1 | 2/2011 | Lucisano et al. |
| 8,133,178 B2 | 3/2012 | Brauker et al. |
| 8,270,661 B2 | 9/2012 | Sorensen et al. |
| 8,357,107 B2 | 1/2013 | Draudt et al. |
| 8,690,820 B2 | 4/2014 | Cinar et al. |
| 8,763,245 B1 | 7/2014 | Lucisano et al. |
| 9,002,711 B2 | 4/2015 | Morinaka et al. |

(56) References Cited

U.S. PATENT DOCUMENTS

| | | |
|---|---|---|
| 9,119,528 B2 | 9/2015 | Cobelli et al. |
| 9,247,901 B2 | 2/2016 | Kamath et al. |
| 9,325,060 B2 | 4/2016 | Kalistaja et al. |
| 9,362,776 B2 | 6/2016 | Low et al. |
| 9,444,027 B2 | 9/2016 | Dibra et al. |
| 9,451,908 B2 | 9/2016 | Kamath et al. |
| 2002/0026108 A1 | 2/2002 | Colvin et al. |
| 2002/0123087 A1 | 9/2002 | Vachon et al. |
| 2002/0156355 A1* | 10/2002 | Gough ............... A61B 5/14532 600/345 |
| 2002/0161286 A1 | 10/2002 | Gerber et al. |
| 2002/0193671 A1 | 12/2002 | Ciurczak et al. |
| 2003/0048621 A1 | 3/2003 | Blood et al. |
| 2003/0049166 A1 | 3/2003 | Pendo et al. |
| 2003/0053784 A1 | 3/2003 | Labrake et al. |
| 2003/0126593 A1 | 7/2003 | Mault |
| 2003/0179167 A1 | 9/2003 | Kolluri et al. |
| 2003/0181794 A1 | 9/2003 | Rini et al. |
| 2003/0187338 A1 | 10/2003 | Say et al. |
| 2003/0217966 A1 | 11/2003 | Tapsak et al. |
| 2003/0228681 A1 | 12/2003 | Ritts et al. |
| 2004/0011671 A1 | 1/2004 | Shults et al. |
| 2004/0012935 A1 | 1/2004 | Tagi et al. |
| 2004/0057043 A1 | 3/2004 | Newman et al. |
| 2004/0064133 A1 | 4/2004 | Miller et al. |
| 2004/0106857 A1 | 6/2004 | Gough et al. |
| 2004/0158194 A1 | 8/2004 | Wolff et al. |
| 2004/0167080 A1 | 8/2004 | Dodge et al. |
| 2004/0176669 A1 | 9/2004 | Colvin et al. |
| 2004/0190111 A1 | 9/2004 | Callies et al. |
| 2004/0199059 A1 | 10/2004 | Brauker et al. |
| 2004/0220459 A1 | 11/2004 | Schlegel et al. |
| 2005/0027175 A1 | 2/2005 | Yang |
| 2005/0031689 A1 | 2/2005 | Shults et al. |
| 2005/0033132 A1 | 2/2005 | Shults et al. |
| 2005/0052858 A1 | 3/2005 | Shima et al. |
| 2005/0059871 A1 | 3/2005 | Gough et al. |
| 2005/0124873 A1 | 6/2005 | Shults et al. |
| 2005/0154271 A1 | 7/2005 | Rasdal et al. |
| 2005/0177036 A1 | 8/2005 | Shults et al. |
| 2005/0196322 A1 | 9/2005 | Truex et al. |
| 2005/0245799 A1 | 11/2005 | Brauker et al. |
| 2005/0245971 A1 | 11/2005 | Brockway et al. |
| 2005/0251083 A1 | 11/2005 | Carr-Brendel et al. |
| 2005/0272989 A1 | 12/2005 | Shah et al. |
| 2006/0085137 A1 | 4/2006 | Bartkowiak et al. |
| 2006/0086624 A1 | 4/2006 | Tapsak et al. |
| 2006/0195029 A1 | 8/2006 | Shults et al. |
| 2006/0204536 A1 | 9/2006 | Shults et al. |
| 2006/0257995 A1 | 11/2006 | Simpson et al. |
| 2006/0257996 A1 | 11/2006 | Simpson et al. |
| 2006/0263763 A1 | 11/2006 | Simpson et al. |
| 2007/0151868 A1* | 7/2007 | Staib ................ A61B 5/1486 205/792 |
| 2008/0033269 A1 | 2/2008 | Zhang |
| 2008/0033272 A1 | 2/2008 | Gough et al. |
| 2008/0039702 A1 | 2/2008 | Hayter et al. |
| 2008/0197024 A1 | 8/2008 | Simpson et al. |
| 2008/0200791 A1 | 8/2008 | Simpson et al. |
| 2008/0317276 A1 | 12/2008 | Sorensen et al. |
| 2009/0281399 A1 | 11/2009 | Keel et al. |
| 2010/0041971 A1 | 2/2010 | Goode, Jr. et al. |
| 2010/0145317 A1 | 6/2010 | Laster et al. |
| 2010/0149042 A1 | 6/2010 | Utsi et al. |
| 2011/0137142 A1 | 6/2011 | Lucisano et al. |
| 2012/0262298 A1 | 10/2012 | Bohm et al. |
| 2012/0283960 A1 | 11/2012 | Budiman |
| 2012/0323100 A1 | 12/2012 | Kamath et al. |
| 2013/0016573 A1 | 1/2013 | Goel et al. |
| 2013/0030273 A1 | 1/2013 | Tapsak et al. |
| 2013/0172692 A1 | 7/2013 | Choi et al. |
| 2013/0178727 A1 | 7/2013 | Hayter et al. |
| 2013/0197332 A1* | 8/2013 | Lucisano ............... A61B 5/0031 600/345 |
| 2014/0046148 A1* | 2/2014 | Simpson ............ A61B 5/14532 600/316 |
| 2014/0309510 A1 | 10/2014 | Lucisano et al. |
| 2014/0323960 A1 | 10/2014 | Sloan |
| 2014/0350652 A1 | 11/2014 | Suwito |
| 2015/0163602 A1 | 6/2015 | Pedersen et al. |
| 2015/0250429 A1 | 9/2015 | Hampapuram et al. |
| 2015/0289823 A1 | 10/2015 | Rack-Gomer et al. |
| 2015/0335285 A1 | 11/2015 | Poon et al. |
| 2016/0022180 A1 | 1/2016 | Joseph et al. |
| 2016/0073964 A1 | 3/2016 | Cobelli et al. |
| 2016/0134980 A1 | 5/2016 | Abolfathi |
| 2016/0163174 A1 | 6/2016 | Zhang |
| 2016/0235300 A1 | 8/2016 | Goodnow |
| 2016/0317744 A1 | 11/2016 | Rule |
| 2017/0173262 A1 | 6/2017 | Veltz |
| 2017/0181628 A1 | 6/2017 | Burnette et al. |
| 2017/0181630 A1 | 6/2017 | Mahalingam et al. |
| 2017/0181674 A1 | 6/2017 | Lucisano et al. |
| 2017/0325725 A1 | 11/2017 | Shah et al. |
| 2017/0357776 A1 | 12/2017 | Baker et al. |
| 2018/0000395 A1 | 1/2018 | Lucisano et al. |
| 2018/0140239 A1 | 5/2018 | Lucisano et al. |
| 2018/0153450 A1 | 6/2018 | Routh et al. |

FOREIGN PATENT DOCUMENTS

| | | |
|---|---|---|
| CN | 101006374 A | 7/2007 |
| CN | 201207090 Y | 3/2009 |
| EP | 0852414 B1 | 11/2004 |
| JP | H11295556 A | 10/1999 |
| JP | 2000121863 A | 4/2000 |
| JP | 2005308982 A | 11/2005 |
| JP | 2007121886 A | 5/2007 |
| WO | WO-9213271 A1 | 8/1992 |
| WO | WO-2008013881 A2 | 1/2008 |
| WO | WO-2011018407 A1 | 2/2011 |
| WO | WO-2011120014 A1 | 9/2011 |
| WO | WO-2013016573 A1 | 1/2013 |
| WO | WO-2014035672 A2 | 3/2014 |

OTHER PUBLICATIONS

Anderson J.M., "Biological Responses to Materials." Annual Review of Materials Research, 2001, vol. 31, pp. 81-110.

Armour J.C., et al., "Application of a Chronic intravascular Blood Glucose Sensor in Dogs," Diabetes, 1990, vol. 39 (12), pp. 1519-1526.

Bard A.J., et al., "Electrochemical Methods: Fundamentals and Applications," 2nd Edition, 2000.

Bilitewski U., et al, "Glucose Biosensors Based on Thick Film Technology," Biosensors and Bioelectronics, 1991, vol. 6, pp. 369-373.

Bremer T.M., et al., "Benchmark Data from the Literature for Evaluation of New Glucose Sensing Technologies," Diabetes Technology and therapeutics, 2001, vol. 3 (3), pp. 409-418.

Cha, C.S., et al., "Electrochemical Behaviour of Microfabricated Thick-film Electrodes," Sensors and Actuators B., 1990, vol. 2, pp. 277-281.

Choleau, et al., "Calibration of a Subcutaneous Amperometric Glucose Sensor Implanted for 7 Days in Diabetic Patients Part 2. Superiority of the One-point Calibration Method," Biosensors and Bioelectronics, 2002, vol. 17, pp. 641-646.

Choleau, et al., "Calibration of a Subcutaneous Amperometric Glucose Sensor Part 1. Effect of Measurement Uncertainties on the Determination of Sensor Sensitivity and Background Current.," Biosensors and Bioelectronics, 2002, vol. 17, pp. 647-654.

Conway M.J., et al., "Radio Telemetry of Blood Po2 in Vivo," Biomedical Engineering, 1973, vol. 8 (10), pp. 428-430.

Data Sheet—Platinum Oxygen Sensor Materials, Component Metallizations, OS1/OS2/OS3, Heraeus.

Data Sheet Cermet Platinum Conductor data sheet, 5542 Print GD, 5542 Pouring GD, Electro-Science Laboratories, Inc.

Data Sheet—4082 and 3804 Platinum Conductors, MEMS Sensor Materials, Ferro Electronic Materials.

(56) References Cited

OTHER PUBLICATIONS

Dutronc, P., et al., "Influence of the Nature of the Screen-printed Electrode Metal on the Transport and Detection Properties of Thick-film Semiconductor Gas Sensors," Sensors and Actuators B, 1992, vol. 6, pp. 279-284.
Fischer U., et al., "A Membrane Combination for Implantable Glucose Sensors. Measurements in Undiluted Biological Fluids," Transactions—American Society for Artificial Internal Organs, 1982, vol. 28, pp. 245-248.
Golonka L.J., et al., "The influence of the Electrode Material on the Sensitivity of an $Sno_2$ Thick-film Gas Sensor," Sensors and Actuators B, 1994, vol. 18-19, pp. 453-456.
Gough D.A., et al., "A Novel Rotated Disc Electrode and Time Lag Method for Characterizing Mass Transport in Liquid-membrane Systems," Journal of the American Institute of Chemical Engineers, 1980, vol. 26, pp. 1013.
Gough D.A., et al., "Membrane-covered, Rotated Disc Electrode," Analytical Chemistry, 1979, vol. 51, pp. 439-444.
Gough D.A., et al., "Two-Dimensional Enzyme Electrode Sensor for Glucose," Analytical Chemistry, 1985, vol. 57 (12), pp. 2351-2357.
Holc J., et al., "Interaction Between Thick-film Platinum Electrodes and Yttria-stabilized $Zro_2$ Ceramic," Journal of Materials Science Letters, 1989, vol. 8, pp. 635-637.
Jablecki M., et al., "Simulations of the Frequency Response of Implantable Glucose Sensors," Analytical Chemistry, 2000, vol. 72 (8), pp. 1853-1859.
Kovatchev B.P., et al., "Graphical and Numerical Evaluation of Continuous Glucose Sensing Time Lag," Diabetes Technology Therapeutics, 2009, vol. 11(3), pp. 139-143.
Leypoldt J.K., et al., "Diffusion and the Limiting Substrate in Two-substrate Immobilized Enzyme Systems," Biotechnology and Bioengineering, 1982, vol. 24 (12), pp. 2705-2719.
Leypoldt J.K., et al., "Model of a Two-substrate Enzyme Electrode for Glucose," Analytical Chemistry, 1984, vol. 56 (14), pp. 2896-2904.
Lucisano, et al., "In Vitro Stability of an Oxygen Sensor," Analytical Chemistry, 1987, vol. 59 (5), pp. 736-739.
Ma, et al., "A Biocompatible and Biodegradable Protein Hydrogel with Green and Red Autofluorescence: Preparation, Characterization and In Vivo Biodegradation Tracking and Modeling," Scientific Reports (Nature.com) published Jan. 27, 2016.
Makale M.T., et al., "Tissue Window Chamber System for Validation of Implanted Oxygen Sensors," American Journal of Physiology. Heart and Circulatory Physiology, 2003, vol. 284 (6), pp. 2288-2294.
McKean B.D. et al., "A Telemetry-Instrumentation System for Chronically Implanted Glucose and Oxygen Sensors," IEEE Transactions on Biomedical Engineering, 1988, vol. 35 (7), pp. 526-532.
Rich A., "Shielding and Guarding," Analog Dialogue, 1983, vol. 17 (1), pp. 8-13.
Sargent B.J., et al., "Design and Validation of the Transparent Oxygen Sensor Array," Biomedical Engineering, IEEE Transactions On, 1991, vol. 38 (5), pp. 476-482.
Elisa Kit Manual Human C3a #550499.
Elisa Kit Manual Human C4a #5550947.
Gough, et al., "Function of an Implanted Tissue Glucose Sensor for More than 1 Year in Animals", Science Translational Medicine, Jul. 28, 2010, vol. 2 (42), pp. 42ra53.
Holmes, et al., Handbook of Thick Film Technology, Electrochemical Publications Ltd (Glasgow: Bell and Bain Ltd., 1976).
Kroschwitz J., "Concise encyclopedia of polymer science and engineering," John Wiley, 1990, pp. 599-1341.
Lucisano, Ph.D. Dissertation, Univ. of Calif. (San Diego), pp. xv-xvi, 8-10, 26-30, 34-36, 96-97 (made available to the public on Dec. 15, 1988)—Call No. "T3.6.L821987".
McNaught A.D., et al., "The Compendium of Chemical Terminology," The Gold Book, Second Edition, Blackwell Science,1997.
Schultz J.S., et al., "Optical Fiber Affinity Sensors," Methods in Enzymology, K. Mosbach, Ed., Academic Press, 1988, vol. 137, pp. 349-366.
West, Electrodeposition and Corrosion Processes, 1971.
Wong CM., et al., "Glucose Oxidase: Natural Occurrence, Function, Properties and Industrial Applications," Applied Microbiology and Biotechnology, 2008, vol. 78 (6), pp. 927-938.
Dhakar L., "Skin Based Flexible Triboelectric Nanogenerators with Motion Sensing Capability," Micro Electro Mechanical Systems (MEMS), 2015 28th IEEE International Conference on, 2015, IEEE, pp. 106-109.
Lemey S., et al., "Wearable Flexible Lightweight Modular RFID Tag With Integrated Energy Harvester," IEEE Transactions on Microwave Theory and Techniques, 2016, vol. 64.7, pp. 2304-2314.
Takei K., et al., "Design for a 400-MHz Passive RFID Prototype System for Long Range Applications," to be published in Proc. IEEE Int. Symp. Antennas Propag. 2007.
Heraeus Technical Data Sheet,Thick Film Materials, Product CL11-5349, retrieved from the Internet on Jun. 14, 2019.
Heraeus Technical Data Sheet,Thick Film Materials, Product CL11-5100, retrieved from the Internet on Jun. 14, 2019.
Heraeus Technical Data Sheet,Thick Film Materials, Product CL11-6109, retrieved from the Internet on Jun. 14, 2019.
Heraeus Technical Data Sheet,Thick Film Materials, Product LP11-4493, retrieved from the Internet on Jun. 14, 2019.
Morris C.G., Definition of "Machine Learning", Academic Press Dictionary of Science and Technology (4th ed.), 1992, Oxford, UK: Elsevier Science & Technology. Retrieved from https://search.credoreference.com/content/entry/apdst/machine_learning/0?institutionId=743.

* cited by examiner

BIOCOMPATIBLE IMPLANTABLE SENSOR APPARATUS AND METHODS

GRANT INFORMATION

This invention was made in part with government support under NIH Grant No. DK-77254. The United States government has certain rights in this invention.

RELATED APPLICATIONS

This application is related to co-owned and U.S. patent application Ser. No. 13/559,475 filed Jul. 26, 2012 entitled "Tissue Implantable Sensor With Hermetically Sealed Housing," and co-pending and co-owned U.S. patent application Ser. No. 14/982,346 filed Dec. 29, 2015 and entitled "Implantable Sensor Apparatus and Methods," each of the foregoing incorporated herein by reference in its entirety. This application is also related to U.S. patent application Ser. No. 10/719,541 filed Nov. 20, 2003, now issued as U.S. Pat. No. 7,336,984 and entitled "Membrane and Electrode Structure for Implantable Sensor," also incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

1. Technical Field

The disclosure relates generally to the field of sensors, therapy devices, implants and other devices which can be used consistent with human beings or other living entities for in vivo detection and measurement or delivery of various solutes, and in one exemplary aspect to methods and apparatus enabling the use of such sensors and/or electronic devices for, e.g. monitoring of one or more physiological parameters, including through use of a novel membrane structure.

2. Description of Related Technology

Implantable electronics is a rapidly expanding discipline within the medical arts. Owing in part to great advances in electronics and wireless technology integration, miniaturization, and performance, sensors or other types of electronics or implantable devices (e.g., therapy agent delivery devices or materials, implants, and the like) which once were beyond the realm of reasonable use in vivo on a living subject can now be surgically implanted within such subjects with minimal effect on the recipient subject, and in fact many inherent benefits.

One particular area of note relates to blood glucose monitoring for subjects, including those with so-called "type 1" or "type 2" diabetes. As is well known, regulation of blood glucose is impaired in people with diabetes by: (1) the inability of the pancreas to adequately produce the glucose-regulating hormone insulin; (2) the insensitivity of various tissues that use insulin to take up glucose; or (3) a combination of both of these phenomena. To correct this disregulation requires blood glucose monitoring.

Currently, glucose monitoring in the diabetic population is based largely on collecting blood by "fingersticking" and determining its glucose concentration by conventional assay. This procedure has several disadvantages, including: (1) the discomfort associated with fingersticking, which should be performed repeatedly each day; (2) the near impossibility of sufficiently frequent sampling (some blood glucose excursions require sampling every 20 minutes, or more frequently, to accurately treat); and (3) the requirement that the user initiate blood collection, which precludes warning strategies that rely on automatic early detection. Using the extant fingersticking procedure, the frequent sampling regimen that would be most medically beneficial cannot be realistically expected of even the most committed patients, and automatic sampling, which would be especially useful during periods of sleep, is not available.

Implantable glucose sensors have long been considered as an alternative to intermittent monitoring of blood glucose levels by the fingerstick method of sample collection. These devices may be partially implanted, where certain components reside within the body but are physically connected to additional components external to the body via one or more percutaneous elements. Partially implanted sensors (discussed in greater detail below) are not viable for long-term use, particularly due to the undesirability of having an essentially open wound on the body for an extended period, and all of the attendant problems associated therewith (including greater risk of infection, the body's natural response to attempt to expel the percutaneous or "through the skin" portion of the implant, etc.).

Implantable sensor devices may alternatively be fully implanted, where all components of the system reside within the body, and there are no percutaneous elements. The operability of one such fully implanted sensor has been demonstrated as a central venous implant in dogs (Armour et al., Diabetes, 39:1519 1526 (1990), incorporated herein by reference in its entirety). Although this sensor provided direct recording of blood glucose, which is most advantageous for clinical applications, the described implantation at a central venous site poses several risks and drawbacks, including risk of blood clot formation and vascular wall damage. An alternative that does not present such risks to the user is to implant the sensor in e.g., a "solid" tissue site and to relate the resulting signal to blood glucose concentration.

Typical sensors implanted in solid tissue sites measure the concentration of solutes, such as glucose, in the blood perfusing the microcirculation in the vicinity of the sensor. Glucose diffuses from nearby capillaries to the sensor surface. Because such diffusion occurs effectively only over very small distances, the sensor responds to the substrate supply only from nearby blood vessels. Conversely, solutes that are generated in the locality of the sensor may be transported away from the sensor's immediate vicinity by the local microvasculature. In either case, the local microcirculation may influence the sensor's response.

Optical glucose sensors are known in the prior art. Schultz and Mansouri disclosed one such version of an optical sensor (J. S. Schultz and S. Mansouri, "Optical Fiber Affinity Sensors," Methods in Enzymology, K. Mosbach, Ed., Academic Press, New York, 1988, vol. 137, pp. 349-366). A variety of other optical techniques including optical coherence tomography, near infrared spectroscopy, Raman spectroscopy, and polarimetry have been tried and failed. Light-based systems using either absorption of light, or emission of light when glucose is "excited" by light have not proven to be accurate since there is no specific light absorption or emission spectrum for glucose. Furthermore, numerous other chemicals or interfering substances in the blood overlap in spectrum with glucose, causing optical methods to be insufficiently specific for glucose monitoring.

A number of electrochemical glucose sensors have also been developed, most of which are based on the reaction catalyzed by glucose oxidase. One such configuration involves the use of glucose oxidase to catalyze the reaction between glucose and oxygen to yield gluconate and hydrogen peroxide. The hydrogen peroxide is either detected directly, or further decomposed by a second enzyme, e.g. catalase, in which case the sensor measures oxygen consumption. In order for glucose oxidase-based sensors to function properly, the presence of excess molecular oxygen relative to molecular glucose is necessary. However, this requirement gives rise to a sensor design problem related to "oxygen deficit," since the concentration of oxygen in subcutaneous tissue is significantly less than that of glucose.

For example, the typical concentration of glucose in the blood is about 4 to about 20 mM, whereas a typical concentration of oxygen in blood plasma may be only about 0.05 to about 0.1 mM. Oxygen concentrations in other tissue fluids may be even lower. As the chemical reaction, and thus, the sensor signal, is limited by the reactant that is present in the sensor's reaction zone at the lowest concentration, an implanted sensor of simple construction would remain limited by oxygen, and would therefore be insensitive to the metabolite of interest (e.g. glucose). Thus, there is a need for differential control of the permeability of the sensor diffusion device (e.g., "membrane") to restrict or modulate the flux of the metabolite of interest (e.g. glucose), and provide a stoichiometric equivalent or excess of oxygen in the reaction zone. The sensor incorporating such a membrane can then be sensitive to the metabolite of interest over the physiologic range. Also, for successful functioning of the implanted sensor, the membrane material exposed to the bodily tissue must further be biocompatible, or elicit a favorable response from the body. Several membrane solutions have been proposed to date.

One such solution has been through the use of macroporous or microporous membranes to ratio the diffusion of oxygen and glucose to the sensing elements, such as that set forth in U.S. Pat. No. 4,759,828 to Young, which discloses use of a laminated membrane with an outer microporous membrane having a pore size of 10 to 125 A (Angstrom) to limit the diffusion of glucose molecules. However, one problem with the use of a macroporous or microporous membrane relates to exposure of the sensing element of the sensor to the environment of the body, which can result in "fouling" or other deleterious effects. Another solution is disclosed in U.S. Pat. No. 4,671,288 to Gough, which describes a cylindrical device, implantable in an artery or vein, which is permeable to glucose only at an end of the device, and with both the curved surface and end permeable to oxygen. In vascular applications, the advantage is direct access to blood glucose, leading to a relatively rapid response. However, a major disadvantage of vascular implantation is the possibility of eliciting blood clots or vascular wall damage, as noted supra.

U.S. Pat. No. 5,660,163 to Schulman discloses another solution through use of a silicone rubber membrane containing at least one "pocket" filled with glucose oxidase in a gelatinous glucose and oxygen-permeable material located over a first working electrode, such that the length of the "pocket" is a multiple of its thickness to optimize the linearity between current and the glucose concentration measurement. However, because the long axis of the "pocket" is oriented parallel to the electrode surface, this design may be less amenable to miniaturization for tissue implantation, and may suffer from yet other disabilities relating thereto.

Still further, another solution has been to utilize a composite membrane that is hydrophilic and also contains small hydrophobic domains to increase the membrane's overall gas solubility, giving rise to differential permeability of glucose and oxygen (e.g. U.S. Pat. Nos. 4,484,987 and 4,890,620 to Gough). However, one salient disadvantage of this approach relates to the requirement that the amount of hydrophobic polymer phase must be relatively large to allow for adequate oxygen permeability. This substantially reduces the hydrophilic volume available for enzyme inclusion sufficient to counter inactivation during long-term operation.

Further, another alternative is described in U.S. Pat. No. 4,650,547 to Gough, which discloses a "stratified" structure in which the electrode was first overlaid with an enzyme-containing layer, and second with a non-glucose-permeable membrane. The resulting structure is permeable to oxygen over a large portion of the surface of the membrane, whereas glucose can only reach the enzyme through the "edge" of the device, thus regulating access of the reactants to the enzyme.

Another significant concern in the context of e.g., implantable solid tissue devices, is the so-called "foreign body response" or FBR, wherein the host's physiology proximate to the implanted sensor is irritated or adversely stimulated into an antibody-modulated or other response which can be deleterious to the operation of the implanted device, especially over longer periods of time. For implanted devices that depend on diffusive transport of solutes to or from the bloodstream (e.g. implanted chemical sensors), such responses can negatively impact device operation due to an increase in mass transfer resistance between the bloodstream and active portions of the device surface resulting from an FBR-mediated development of fibrous tissue surrounding the device. The FBR also can complicate explants of the implanted device (due to, e.g., the FBR causing significant encapsulation of the implanted device, thereby increasing its effective size when explanted), and result in yet other disabilities. Thus, accounting for (and minimizing) the FBR remains an important consideration for literally any implanted device. Some prior art solutions for implantable sensors have attempted to use layers external to the sensing enzyme region to actively modulate or eliminate the FBR. Such approaches have typically used materials for such layer(s) which are designed to encourage blood vessel growth and perfusion in the vicinity of the sensor or into the layer(s), which is undesirable, because such modulated responses are often not predictable and furthermore may not be sustainable for extended durations.

Accuracy is also an important consideration for implanted analyte sensors, especially in the context of blood glucose monitoring. Hence, ensuring accurate measurement for extended periods of time (and minimizing the need for any other confirmatory or similar analyses) is of great significance.

Similarly, having adequate dynamic range for the implanted sensor is important, particularly as it relates to accuracy. Simply stated, the implanted sensor device should be able to accurately measure the target analyte over the entire normal (or even abnormal) range of values that may be encountered within the host's physiology.

As such, there is a compelling need for apparatus and methods directed to an implantable analyte (e.g., glucose) sensor designed to overcome the "oxygen deficit" problem and the disadvantages associated with the prior art devices discussed above (including FBR), while maintaining a high degree of accuracy (including over a broad dynamic range), and robustness for extended periods of time. Methods of reliably manufacturing such sensors are also needed.

SUMMARY

The present disclosure satisfies the foregoing needs by providing, inter alia, improved apparatus and associated methods for in vivo glucose monitoring, including for example within an implantable sensor apparatus or other electronic device within a living subject.

In a first aspect of the disclosure, a sensor apparatus is disclosed. In one embodiment, the sensor apparatus is configured for (full) implantation in e.g., the solid tissue of a living being, and includes one or more sensor elements capable of measuring blood glucose level with a prescribed range of response. In one variant, each sensor element includes a hydrophobic outer membrane element, a non-enzymatic membrane, and an enzyme matrix, and the range of response (at a given oxygen level) of each sensor element is selectable or controllable through control of one or more physical attributes of the non-enzymatic membrane and a "spout" structure formed therein (e.g., base height, base diameter, spout height, and/or spout diameter).

In one implementation, the outer membrane is comprised at least in part of a silicone rubber compound, and a single parameter of those listed above (e.g., the spout diameter) is modified to effect the desired range of response.

In one variant of the foregoing implementation, the non-enzymatic membrane comprises a crosslinked albumin material that is substantially permeable to at least glucose and oxygen present at the outer surface thereof. The non-enzymatic membrane is also placed in contact with a top surface of the enzyme material so as to permit diffusion of the oxygen and glucose into the enzyme material to permit chemical interaction therein, while affording the solid tissue of the host an unreactive "buffer zone," thereby isolating the host tissue from direct contact with the enzyme material.

In another variant, the response time (at a given oxygen level) of each sensor element is selectable or controllable through control of one or more physical attributes of the non-enzyme membrane and/or its surrounding "spout" structure (e.g., base height, spout height, and/or non-enzyme membrane thickness).

In one implementation, the outer membrane is comprised at least in part of a silicone rubber compound, the non-enzyme membrane comprises an albumin-based compound, and a single parameter of those listed above (e.g., the spout height) is modified to effect the desired response time (or rate of response).

In another variant, the sensor apparatus includes one or more sensor elements capable of measuring blood glucose level both (i) within a prescribed range of response and (ii) within a prescribed time period. Each sensor element includes a non-enzymatic membrane element (e.g., including crosslinked albumin), the range of response (at a given oxygen level) of the sensor element(s) is selectable or controllable through control of base diameter and/or spout diameter, and the rate or timing of response (at a given oxygen level) of the sensor element(s) is selectable or controllable through control of base height and/or spout height.

In another embodiment, the sensor apparatus includes: signal processing circuitry and at least one detector element in signal communication with the signal processing circuitry. The at least one detector element includes: a substantially enclosed cavity, the substantially enclosed cavity comprising at least one enzymatic substance, and at least one aperture in communication with the cavity; an electrolyte layer; at least one electrode disposed at least partly within or contacting the electrolyte layer; and a non-enzymatic membrane at least partly occluding the aperture, the non-enzymatic membrane comprising a material at least partly permeable to an analyte yet which does not exacerbate an FBR (including fibrous tissue growth). In one variant, the non-enzymatic membrane comprises a crosslinked albumin-based material, and the at least one detector element is configured to utilize chemical interaction between at least the analyte and the enzymatic substance to enable generation of an electrical signal at the electrode via the electrolyte layer, the electrical signal relating to a concentration of the analyte in a region external to the cavity and the membrane.

In a second aspect, a method of forming a sensor element for use on, inter alia, an implantable sensor apparatus is disclosed. In one embodiment, the method includes forming the aforementioned outer hydrophobic membrane of the sensor element using a molding process, such that the desired parameter value(s) is/are achieved (e.g., desired aperture placement and diameter), and disposing an enzymatic material within an interior cavity of the sensor element, as well as a non-enzymatic tissue-contacting layer over top of the enzymatic material and within the aperture. In one variant, the outer membrane comprises a silicone rubber compound that can be molded according to the foregoing methodology, and the non-enzymatic tissue-contacting layer includes albumin. The albumin layer is in one implementation configured to mitigate excessive FBR.

In a third aspect, a method of configuring a sensor apparatus to achieve a desired level of performance is disclosed. In one embodiment, the sensor apparatus includes one or more elements with permeable membranes, and the method includes configuring one or more parameters relating to the membrane(s) to achieve the desired level of performance. In one variant, the level of performance relates to a detection range of response of glucose concentration in the blood of a living being, and the one or more parameters comprise a diameter or an area associated with at least a portion of the permeable membrane(s), and/or its thickness.

In another aspect, a membrane useful with an in vivo sensor apparatus is disclosed. In one embodiment, the membrane is formed at least in part of a crosslinked albumin-based compound, and the membrane is specifically configured with respect to at least one parameter thereof (e.g., height relative to a base, thickness, and/or diameter, etc.) to produce a desired level of performance or response with respect to one or more substances (e.g., glucose in blood), such as rate of permeation of glucose through the membrane, or detectable range of concentrations of the enzyme. In one variant, the albumin-based membrane is configured so as not to exacerbate an FBR after implantation of the host sensor apparatus.

In another aspect of the disclosure, a sensor apparatus with heterogeneous sensor elements is disclosed. In one embodiment, the sensor apparatus is configured for (full) implantation in e.g., the solid tissue of a living being, and includes two or more sensor elements capable of measuring blood glucose level in at least one of: (i) different ranges of response, and/or (ii) different times or rates of response. In one variant, each sensor element includes a non-enzymatic membrane element in contact with the solid tissue, and the range of response (at a given oxygen level) of each sensor element is selectable or controllable through control of one or more physical attributes of the membrane and/or its surrounding "spout" structure (e.g., base diameter and and/ or spout diameter). The two or more sensor elements utilize membranes having respective different ranges of response due to e.g., different physical diameters thereof.

In another implementation, the different ranges of response to glucose level at least partly overlap one another. In yet another implementation, the different ranges of response to glucose level are substantially contiguous, but do not significantly overlap one another. In yet a further implementation, the different ranges of response to glucose level are neither contiguous or overlap one another; i.e., are separated by one or more ranges (e.g., those not of interest).

In another variant, each sensor element includes a non-enzymatic membrane element (e.g., an albumin-based membrane such as that referenced supra), and the time or rate of response (at a given oxygen and glucose level) of each sensor element is selectable or controllable through control of one or more physical attributes of the membrane and/or its surrounding "spout" structure (e.g., membrane thickness, and/or height of the spout above a base region). The two or more sensor elements utilize non-enzyme membranes having respective different rates of response due to e.g., different physical diameters or other properties thereof. In one implementation, eight (8) sensor elements are included on the sensor apparatus, two (2) of which are configured to measure glucose level within a first range of times, and two of which are configured to measure glucose level within a second range of times; the remaining four (4) sensor elements are used to measure oxygen concentration (i.e., are reference elements).

In another variant, combinations of the foregoing are utilized; e.g., the sensor apparatus includes sensor elements having heterogeneity with respect to both range of response (concentration) and rate of response (rate of permeation).

In yet a further aspect of the disclosure, a sensor element configuration is disclosed. In one embodiment, the sensor element is used as part of an implantable sensor apparatus, and the configuration includes an enzyme-free outer layer or portion which prevents tissue of the host being from contacting immobilized underlying enzymes (e.g., glucose oxidase and catalase) within the sensor element when the sensor element is in vivo, thereby both (i) mitigating or eliminating a foreign body response (FBR) within the tissue due to lack of exposure to the enzymes or byproducts of the underlying reaction (e.g., peroxide), and (ii) ultimately enhancing operation and longevity of the sensor apparatus due to, inter alia, the aforementioned lack of FBR and the (excess) immobilized enzymes. In one variant, the enzyme-free outer layer or portion comprises a soluble protein-based (e.g., albumin-based) material which is cured using a cross-linking agent, and which is configured so as not to encourage blood vessel growth into the membrane after implantation of the sensor element into a living host.

In a further aspect of the disclosure, a method of mitigating foreign body response (FBR) associated with an implanted analyte detector element is disclosed. In one embodiment, the method includes creating an enzyme-free buffer zone between a reactive enzymatic portion of the detector element using a non-enzymatic membrane or layer that is permeable to both the analyte (e.g., glucose) and oxygen. In one variant, the enzymatic portion comprises a mechanically stable matrix, such that the enzymes of the matrix are substantially immobilized and do not migrate outward toward the host's tissue through the non-enzymatic membrane or layer, but the analyte and oxygen from the tissue can migrate inward. In one implementation, the non-enzymatic membrane material is selected so as to not exacerbate the FBR, thereby mitigating fibrous tissue formation and making subsequent explants of the detector element easier due to limited FBR-induced encapsulation.

In another aspect, a method of controlling at least one operating characteristic of an oxygen-based blood analyte sensing element is disclosed. In one embodiment, the sensing element has an enzyme-filled cavity with a base region, the cavity accessible via an aperture and an at least partly protein-based permeable membrane covering the aperture, and the method includes controlling at least one of a dimension of the aperture or the base so as to selectively control the diffusion of analyte and oxygen into the cavity, thereby causing the sensing element to exhibit the desired operating characteristic when operated. In one variant, the analyte comprises glucose; the enzyme filling comprises glucose oxidase and catalase; and the desired operating characteristic comprises a range of analyte concentration that can be detected by the sensing element, and the at least one dimension comprises at least one of: (i) a diameter of the aperture, and/or (ii) a diameter of the base region.

In another variant, the analyte comprises glucose; the enzyme filling comprises glucose oxidase and catalase; and the desired operating characteristic comprises a time within which an analyte concentration can be detected by the sensing element, and the at least one dimension comprises at least one of: (i) a height of the aperture relative to a height of the base region.

In yet a further aspect of the disclosure, a method of operating an oxygen-based blood analyte sensing element is described. In one embodiment, the element includes an enzyme-filled cavity with a base region, the cavity accessible via an aperture and an at least partly enzyme-free permeable membrane covering the aperture, and the method includes: selectively controlling the migration of at least an analyte into the cavity through the enzyme-free membrane; creating residual oxygen within the cavity; and selectively controlling the migration of at least portions of the residual oxygen to at least one electrode of the sensing element. In one variant, the selective control of the migration of analyte and the selective control of the migration of oxygen cooperate to cause the sensing element to exhibit a desired operating characteristic.

In one implementation, the desired operating characteristic comprises a range of glucose concentrations detectable by the sensing element, and the selectively controlling the migration of the glucose is accomplished at least in part by selectively choosing an area of the aperture.

In still another aspect, an analyte detection apparatus is disclosed. In one embodiment, the apparatus includes: a substrate; at least one electrode disposed on or within the substrate, the at least one electrode comprising at least a terminal configured to enable electrical signals to be communicated from the electrode to a circuit; an electrolyte material in communication with at least a portion of the at least one electrode; a first membrane element in contact with at least a portion of the electrolyte material; a second membrane element comprising a cavity formed therein, and at least one aperture; an enzymatic material disposed within the cavity and configured to interact with the analyte and at least a portion of the oxygen entering the cavity via the aperture; and a non-enzymatic material configured to substantially occlude the aperture and frustrate migration of any enzymes from the enzymatic material outward to the tissue of the living host, yet permit diffusion of analyte and oxygen therethrough. In one variant, a response characteristic of the analyte detection apparatus is controlled at least in part by a shape of the second membrane element.

In another variant, the substrate comprises a ceramic material, the first membrane comprises a polymeric material, and the second membrane element comprises a silicone rubber-based material; the analyte comprises glucose, and the enzymatic material comprises glucose oxidase and catalase disposed in a crosslinked matrix; and the non-enzymatic material comprises albumin.

In a further aspect of the disclosure, a dynamically variable sensor apparatus is disclosed. In one embodiment, the sensor apparatus includes: signal processing circuitry; and at least one first detector element and at least one second detector element each in signal communication with the signal processing circuitry. In one variant, the at least one first and second detector elements each comprise: a partly enclosed cavity, the cavity comprising at least one enzymatic substance, and at least one aperture in communication with the cavity, the aperture at least partly obscured with a non-enzyme yet permeable substance; an electrolyte layer; and at least one electrode disposed at least partly within or contacting the electrolyte layer; and the at least one first and second detector elements are each configured to utilize chemical interaction between at least the analyte and their respective enzymatic substance to enable generation of an electrical signal at their respective electrodes via their respective electrolyte layer, the electrical signal relating to a concentration of the analyte in a region external to their respective cavities.

In one implementation, at least one of (i) a shape or dimension of the aperture, (ii) a thickness of the non-enzyme yet permeable substance, and/or (iii) a shape or dimension of the cavity, for the at least one first detector element is different from that for the second at least one detector element, thereby enabling the at least one first detector element and the at least one second detector element to have a different operational characteristic from the other.

In yet another aspect of the disclosure, a method of mitigating a foreign body response (FBR) within a living being while monitoring blood glucose level using an implanted sensor apparatus is described. In one embodiment, the method includes: allowing at least oxygen molecules and glucose molecules from the living being's blood to permeate through a non-enzymatic layer or membrane to an enzyme-containing material with which the oxygen molecules and glucose molecules can chemically interact, the chemical interaction enabling the monitoring; and at least mitigating egress of enzymes within the enzyme-containing material outward through the layer or membrane. In one variant, the non-enzymatic material comprises a protein-based (e.g., albumin) substance which is chemically cross-linked, and which does not encourage blood vessel growth into its thickness.

In a further aspect, a method of manufacturing an analyte detector element is described. In one embodiment, the method includes: providing a substrate; embedding at least one electrode within the substrate; disposing an electrolyte over at least a portion of the substrate, including at least a portion of the electrode; forming an inner membrane over at least a portion of the electrolyte; forming an outer membrane having an aperture formed therein, and disposing the outer membrane over the inner membrane such that the inner and outer membranes form a cavity; disposing an enzyme matrix material into the cavity such that it at least contacts the inner membrane and aperture; and forming a layer of non-enzymatic material within the aperture such that it at least partly contacts the enzyme matrix material.

In one variant of the method, the outer and inner membranes comprise an elastomeric material (e.g., silicone rubber), and the outer membrane is adhered (e.g., via a room temperature vulcanizing (RTV) adhesive) to the inner membrane in order to create the cavity. The enzyme matrix is then introduced into the cavity via the aperture; e.g., the matrix is substantially liquefied, and is poured or piped into the cavity so as to substantially fill the cavity, and exclude air therefrom, while also maintaining the aperture region entirely enzyme-free. The enzyme matrix is then cured (e.g., chemically crosslinked), and subsequently the non-enzymatic material (also in a substantially liquefied or flowable form) is poured or piped into the top portion of the cavity via the aperture (i.e., atop the cured enzyme matrix), and subsequently chemically crosslinked as well.

Other features and advantages of the present disclosure will immediately be recognized by persons of ordinary skill in the art with reference to the attached drawings and detailed description of exemplary embodiments as given below.

Figure 1:
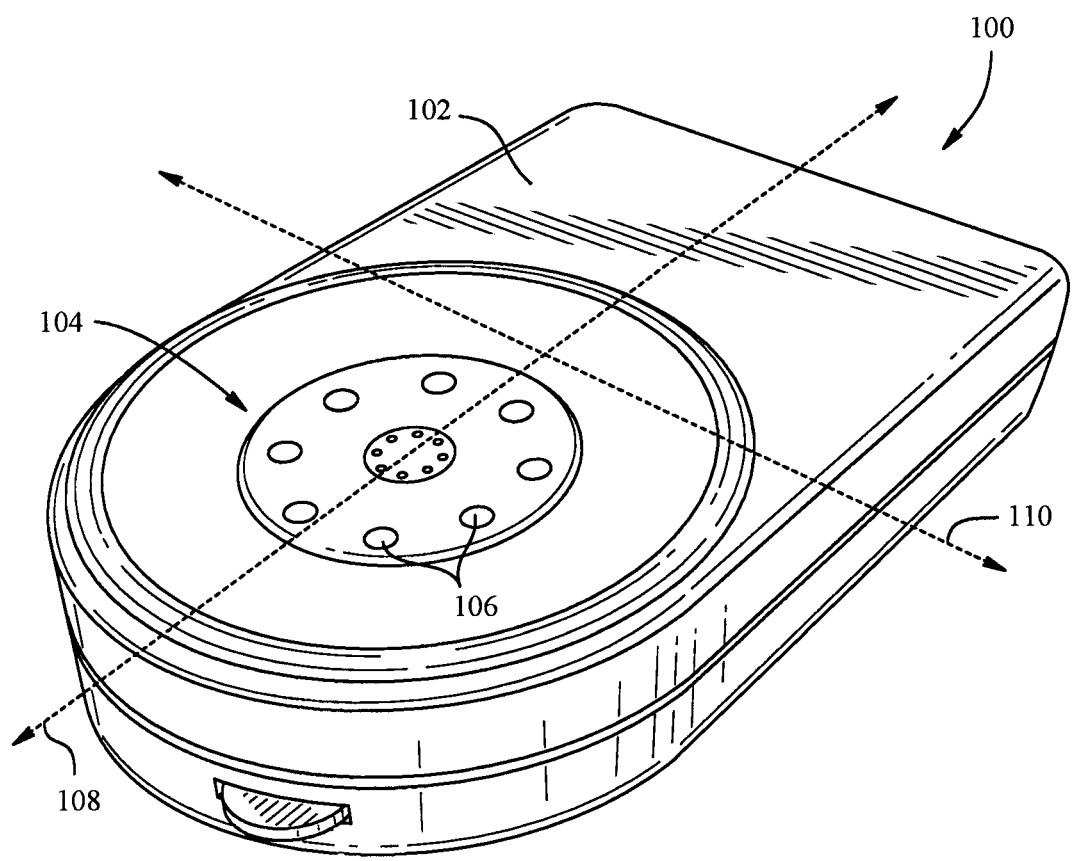
FIG. 1 is a front perspective view of one exemplary embodiment of a fully implantable sensor apparatus according to the present disclosure.
Figure 1A:
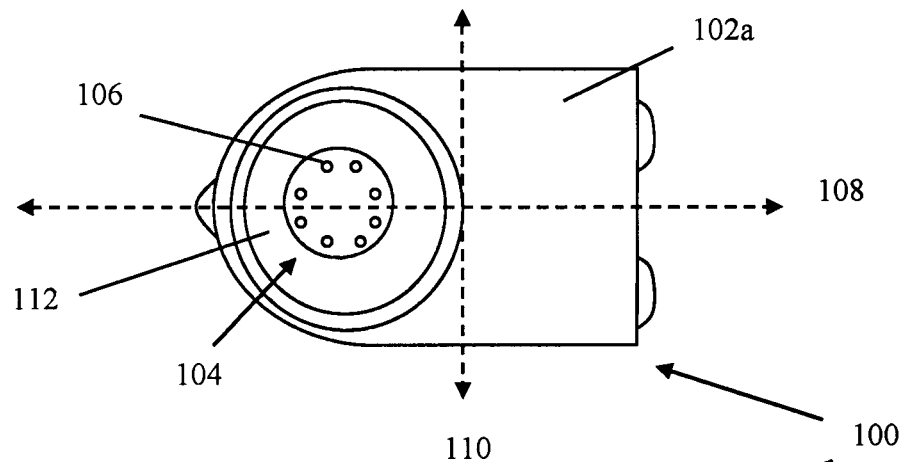
FIGS. 1A-1C are top, bottom, and side elevation views, respectively, of the exemplary sensor apparatus of FIG. 1.
Figure 1B:
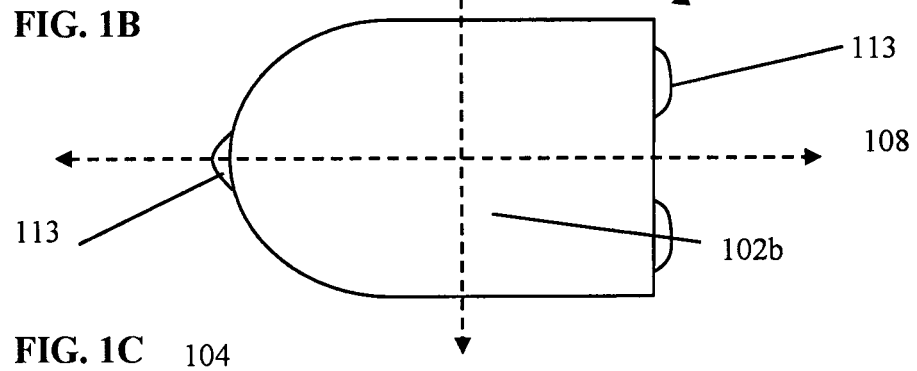

All Figures © Copyright 2016 GlySens Incorporated. All rights reserved.

DETAILED DESCRIPTION

Reference is now made to the drawings, wherein like numerals refer to like parts throughout.

Detailed Description of Exemplary Embodiments

Exemplary embodiments of the present disclosure are now described in detail. While these embodiments are primarily discussed in the context of a fully implantable glucose sensor, such as those exemplary embodiments described herein, and/or those set forth in U.S. Patent Application Publication No. 2013/0197332 filed Jul. 26, 2012 entitled "Tissue Implantable Sensor With Hermetically Sealed Housing;" U.S. Pat. No. 7,894,870 to Lucisano et al. issued Feb. 22, 2011 and entitled "Hermetic implantable sensor;" U.S. Patent Application Publication No. 20110137142 to Lucisano et al. published Jun. 9, 2011 and entitled "Hermetic Implantable Sensor;" U.S. Pat. No. 8,763,245 to Lucisano et al. issued Jul. 1, 2014 and entitled "Hermetic feedthrough assembly for ceramic body;" U.S. Patent Application Publication No. 20140309510 to Lucisano et al. published Oct. 16, 2014 and entitled "Hermetic Feedthrough Assembly for Ceramic Body;" U.S. Pat. No. 7,248,912 to Gough, et al. issued Jul. 24, 2007 and entitled "Tissue implantable sensors for measurement of blood solutes;" and U.S. Pat. No. 7,871,456 to Gough et al. issued Jan. 18, 2011 and entitled "Membranes with controlled permeability to polar and apolar molecules in solution and methods of making same," each of the foregoing incorporated herein by reference in its entirety, it will be recognized by those of ordinary skill that the present disclosure is not so limited. In fact, the various aspects of the disclosure are useful with, inter alia, other types of implantable sensors and/or electronic devices.

Further, while the following embodiments describe specific implementations of e.g., oxygen-based multi-sensor element devices, and having specific configurations, those of ordinary skill in the related arts will readily appreciate that such descriptions are purely illustrative, and in fact the methods and apparatus described herein can be used consistent with, and without limitation: (i) in living beings other than humans; (ii) other types or configurations of sensors (e.g., peroxide-based glucose sensors, or sensors other than glucose sensors, such as e.g., for other analytes such as urea, lactate); and/or (iii) devices intended to deliver substances to the body (e.g. implanted drug pumps, drug-eluting solid materials, and encapsulated cell-based implants, etc.); and/ or other devices (e.g., non-sensors and non-substance delivery devices).

As used herein, the terms "detector" and "sensor" refer without limitation to a device that generates, or can be made to generate, a signal indicative of a measured parameter, such as the concentration of an analyte (e.g., glucose or oxygen). Such a device may be based on electrochemical, electrical, optical, mechanical, thermal, or other principles as generally known in the art. Such a device may consist of one or more components, including for example, one, two, three, or four electrodes, and may further incorporate immobilized enzymes or other biological or physical components, such as membranes, to provide or enhance sensitivity or specificity for the analyte.

As used herein the term "membrane" refers without limitation to a substance, layer or element configured to have at least one desired property relative to the aforementioned analyte, such as e.g., a permeability to a given type of analyte or sub stance.

As used herein, the terms "enzyme free" and "non-enzymatic" include, without limitation, materials that are completely enzyme-free, and materials that are substantially enzyme free (e.g., may have a small percentage of residual or unintentional enzymes).

Likewise, as used herein, the terms "top," "bottom," "side," "up," "down," and the like merely connote, without limitation, a relative position or geometry of one component to another, and in no way connote an absolute frame of reference or any required orientation. For example, a "top" portion of a component may actually reside below a "bottom" portion when the component is mounted to another device (e.g., host sensor).

Overview

In one exemplary aspect, the present disclosure provides improved enzymatic detectors and associated membrane apparatus, and associated methods of manufacturing and use, such as within a fully implantable sensor apparatus of the type described in U.S. patent application Ser. No. 14/982,346 entitled "Implantable Sensor Apparatus and Methods," previously incorporated by reference herein. Advantageously, the apparatus and methods of the disclosure enable, inter alia, substantially continuous, long-term and accurate monitoring of blood glucose levels in living beings using the aforementioned implantable sensor apparatus, without the need for prior art "finger sticks," transcutaneous apparatus worn on external surfaces of the body, or intravenous devices, each having their own disabilities as previously described.

Specifically, the present disclosure describes a novel sensor (detector) element configuration, including use of selectively configured membrane elements and enzyme region shapes, which enable accurate detection of blood glucose level within the solid tissue of the host for extended periods of time, and within desired ranges and/or rates of response. The performance of the detector elements may be controlled through variation of one or more physical parameters of the membrane elements (e.g., dimensions, shapes, etc.), including an access or "spout" region, so as to allow for precise measurement of the target analyte, while also maintaining isolation between the host's tissue and the underlying enzymes and also potentially between the host tissue and reaction byproducts used in the sensor element, thereby advantageously minimizing foreign body response (FBR) to the device while implanted, particularly in the region(s) where sensing of the target analyte is performed.

In one approach, an enzyme-free layer or membrane is formed within the spout region and used in conjunction with a substantially immobilized underlying enzyme material, such that the analyte (e.g., glucose molecules) and oxygen molecules can permeate through to the enzyme region, but the enzymes (e.g., catalase and glucose oxidase) do not permeate outward. The spout region of the sensor element is also advantageously maintained substantially enzyme-free during manufacturing, and a reasonably tight "seal" is formed around a periphery of the enzyme-free layer or membrane after curing (and the enzyme-free layer may even be bonded to its surrounding structure), such that undesired enzyme migration or contact with the living host's tissue are avoided.

The disclosed configuration (including use of the enzyme-free layer) advantageously does not encourage blood vessel ingrowth, which inter alia, enables accurate sensor apparatus operation during periods of extended implantation. By not encouraging such ingrowth, otherwise unstable/unpredictable modulation of FBR to the extent required to encourage blood vessel ingrowth is wholly avoided. In one variant, such ingrowth is frustrated (or not encouraged) through selective control of pore sizes within the non-enzymatic layer.

Control of response range and/or rate also permits easy "customization" of sensor elements, whether on a per-element or per-sensor apparatus basis. For example, the techniques of the present disclosure allow for ready construction of an implantable sensor apparatus having multiple heterogeneous detector elements with respective multiple ranges of sensitivity and/or rates of detection, thereby extending the dynamic range of the sensor apparatus (both in terms of analyte concentration and/or time, as desired).

Moreover, in one variant, the various heterogeneous detector elements can be selectively switched on/off (even while the sensor apparatus is in vivo), so as to, e.g., accommodate "on the fly" changes to blood glucose concentration occurring within the host, or to maintain the detector elements within a known or desirable range of accuracy or sensitivity.

Methods of manufacturing the aforementioned membranes and sensor elements are also disclosed herein.

Exemplary Implantable Sensor Apparatus

Figure 1C:
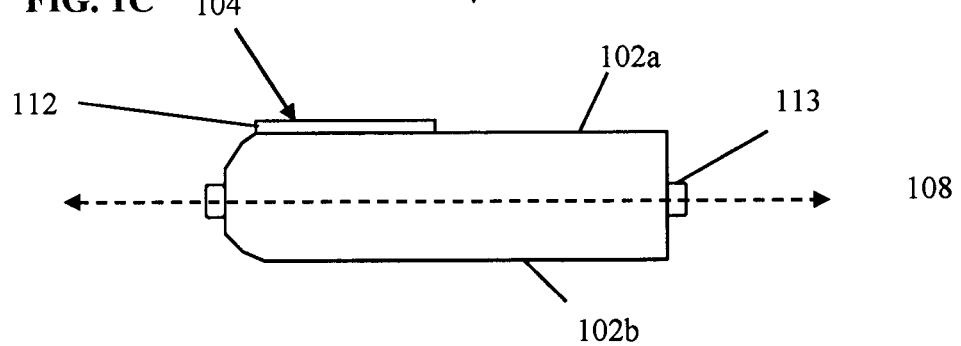

Referring now to FIGS. 1-1C, one exemplary embodiment of a sensor apparatus useful with various aspects of the present disclosure is shown and described.

As shown in FIGS. 1-1C, the exemplary sensor apparatus 100 comprises a somewhat planar housing structure 102 with a sensing region 104 disposed on one side thereof (i.e., a top face 102a). The exemplary substantially planar shape of the housing 102 provides mechanical stability for the sensor apparatus 100 after implantation, thereby helping to preserve the orientation of the apparatus 100 (e.g., with sensing region 104 facing away from the epidermis and toward the proximate fascial layer), resisting rotation around its longitudinal axis 108, and translation, or rotation about its transverse axis 110, which might otherwise be caused by e.g., normal patient ambulation or motion, sudden accelerations or decelerations (due to e.g., automobile accidents, operation of high-performance vehicles such as aircraft), or other events or conditions. Notwithstanding, the present disclosure contemplates sensor apparatus of shapes and/or sizes other than that of the exemplary apparatus 100, including use of means to maintain the desired orientation and position such as e.g., protruding tabs, "anchoring" the sensor apparatus to surrounding physiological structures such as the fascial layer by means of sutures or the like, attached tissue ingrowth structures, and so forth.

The exemplary sensor apparatus of FIGS. 1-1C further includes a detector array 104 comprising a plurality of individual detectors elements 106 on the top face 102a of the sensor apparatus housing 100. In exemplary embodiments, the detector array 104 of the present invention includes eight (8) detector elements 106 with associated membranes (not shown) disposed on a detector substrate 112 (e.g. ceramic disk), which function as a group. As will be discussed in greater detail infra, the detector elements 106 in the illustrated embodiment comprise a plurality of primary detectors including associated membranes containing glucose oxidase and catalase to measure glucose-dependent oxygen levels, and a plurality of secondary detectors including associated membranes without bonded enzymes to measure background oxygen levels.

In operation, a signal-processing element (not shown) measures the current difference between the glucose-dependent oxygen current and the background oxygen current, to produce a glucose-dependent difference current. As such, the exemplary sensor apparatus 100 of the present disclosure utilizes an "oxygen-sensing differential measurement," by comparison of the glucose-dependent oxygen signal to the background oxygen signal that produces, upon further signal processing, a continuous real-time blood glucose concentration measurement. It will be appreciated, however, that the methods and apparatus described herein are in no way limited to such "differential" schemes.

The exemplary sensor apparatus of FIGS. 1-1C also includes a plurality (three in this instance) of tabs or anchor apparatus 113 disposed substantially peripheral on the apparatus housing. These anchor apparatus provide the implanting surgeon with the opportunity to anchor the apparatus to the anatomy of the living subject, so as to frustrate translation and/or rotation of the sensor apparatus 200 within the subject immediately after implantation but before any body response (e.g., FBR) of the subject has a chance to immobilize (such as via encapsulation) the sensor apparatus. See, e.g., the exemplary apparatus and techniques described in co-owned and co-pending U.S. patent application Ser. No. 14/982,346 filed Dec. 29, 2015 and entitled "Implantable Sensor Apparatus and Methods," incorporated herein by reference in its entirety.

In the exemplary configuration, four (4) of each type of detector elements 106 are included (i.e., four primary, and 4 secondary), although it will be appreciated that any number of detector elements can be used consistent with the disclosure (including in pairs, or where one primary or secondary detector is used in conjunction with two or more of the other type of detector). Numerous permutations are possible, all considered within the scope of the present disclosure.

Further considerations relating to the total number of detector elements 106 on the detector array 104 include, e.g., available surface area of the detector substrate 112, which in turn is dictated by a desire to minimize the overall size of the sensor for implantation. In the exemplary embodiments of the sensor apparatus 100, use of a plurality of detector elements 106 is important to: 1) maximize the probability that several detectors will be positioned very near an active vascular bed; 2) afford the possibility of ignoring a given detector element if it operates inaccurately, erratically, or becomes nonresponsive over time; and 3) minimize the effects of local variations in analyte concentration, as well as local variations in the magnitude of any confounding phenomena occurring proximate the detector elements (see, inter alia, U.S. Pat. No. 7,248,912 previously incorporated herein, for a discussion of various confounding phenomena).

The exemplary detector elements 106 are of the enzyme-electrode type (some utilizing membranes containing immobilized glucose oxidase and catalase), such as those exemplary embodiments described herein, and/or those set forth in U.S. Pat. No. 4,484,987 to Gough, entitled "Method And Membrane Applicable To Implantable Sensor;" U.S. Pat. No. 4,671,288 to Gough, entitled "Electrochemical Cell Sensor For Continuous Short-Term Use In Tissues And Blood;" U.S. Pat. No. 4,650,547 to Gough, entitled "Method And Membrane Applicable To Implantable Sensor;" U.S. Pat. No. 4,890,620 to Gough, entitled "Two-Dimensional Diffusion Glucose Substrate Sensing Electrode;" U.S. Pat. No. 5,322,063 to Allen et al. entitled "Hydrophilic Polyurethane Membranes For Electrochemical Glucose Sensors;" U.S. Pat. No. 5,660,163 to Schulman et al., entitled "Glucose Sensor Assembly," and U.S. Pat. No. 6,721,587 to Gough, entitled "Membrane and Electrode Structure For Implantable Sensor," each of which are incorporated herein by reference in its entirety. It will be appreciated, however, that the type and operation of the sensor apparatus 100 may vary; i.e., other types of detector elements/sensor apparatus, configurations, and signal processing techniques thereof may be used consistent with the various aspects of the present disclosure, including, for example, signal processing techniques based on various combinations of signals from individual elements in the otherwise spatially-defined sensing elements pairs.

Methods for calculating the levels of glucose present based on a specific enzymatic reaction are well known in the art, as are certain calibration techniques (see, e.g., Choleau, et al., Biosens. Bioelectron., 17:647-654 (2002) and Choleau, et al., Biosens. Bioelectron., 17:641-646 (2002), the teachings of which are incorporated herein by reference in their entirety). Benchmark data for evaluation of sensor performance are also available (Bremer, et al, Diabetes Technol. Ther., 3:409-418 (2001), the teachings of which are incorporated herein by reference).

The exemplary detector elements 106 utilize the following two-step chemical reaction catalyzed by glucose oxidase and catalase to detect glucose, as described in Armour et al. (Diabetes 39, 1519-1526 (1990)):

$$Glucose + O_2 + H_2O \rightarrow Gluconate + H_2O_2 \text{ (Glucose Oxidase)}$$

$$H_2O_2 \rightarrow \tfrac{1}{2}O_2 + H_2O \text{ (Catalase)}$$

$$Glucose + \tfrac{1}{2}O_2 \rightarrow Gluconate \text{ (Net)}$$

In the exemplary embodiment of the (primary) detector elements described herein, the two enzymes (glucose oxidase and catalase) are entrapped or more preferably immobilized within a gel matrix (discussed infra) that is e.g., crosslinked for mechanical and chemical stability, and which is in operative contact with a working electrode to electrochemically detect oxygen. It will be appreciated that while a chemical or other crosslinking technique can be used consistent with the disclosure to immobilize the enzymes, other approaches for immobilization and/or mechanical stabilization of the enzyme matrix (primary detectors) and/or non-enzyme matrix (secondary detectors) may also be used, whether alone or in combination with the foregoing. For instance, in one variant, a non-cross-linked (yet mechanically stable) gel could be used. As another alternative, a porifera or other sponge/sponge-like structure could be used (e.g., with the enzyme disposed within the pores or ostia of the structure for mechanical stability). In yet another approach, a ladder, scaffold, or three-dimensional mesh structure could be used to support the enzymatic material.

In the illustrated embodiment, glucose and ambient oxygen diffuse into the gel matrix and encounter the enzymes, the above reactions occur, and the oxygen that is not consumed in the process is detected by the working or primary electrode.

Exemplary Detector Element with Associated Membranes

Figure 2:
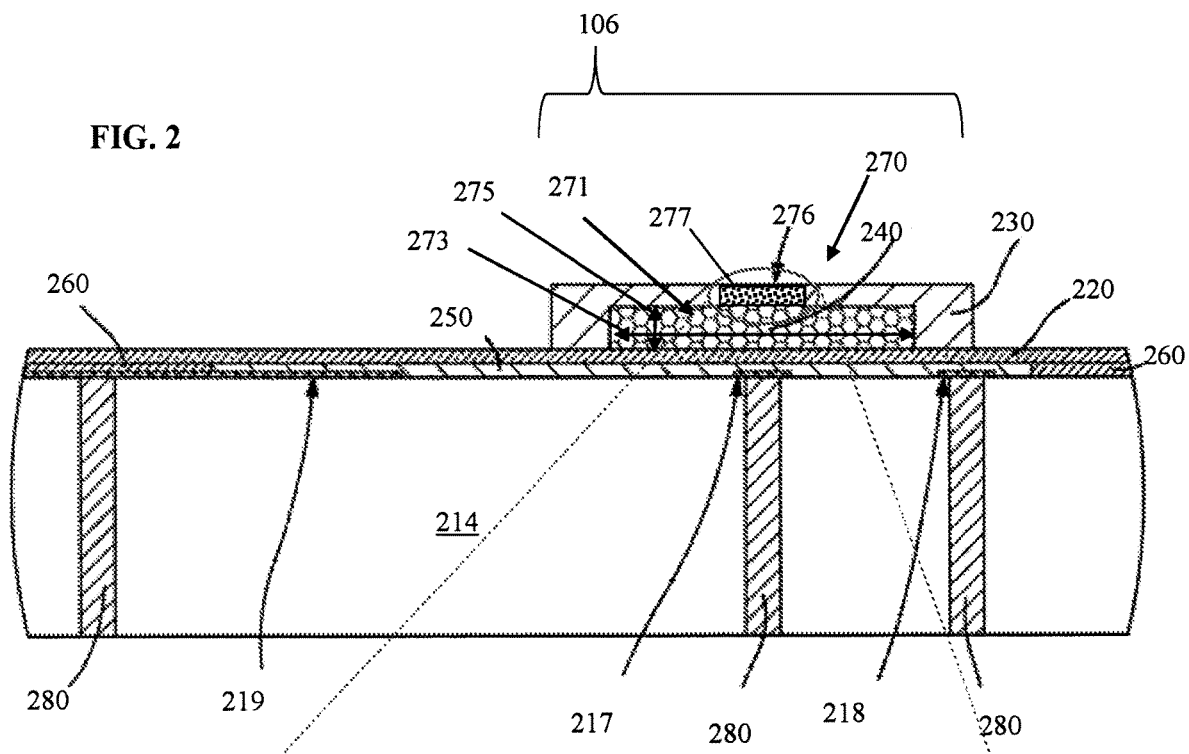
FIG. 2 is a side cross-sectional view of one exemplary detector element of a detector array in a fully implantable sensor apparatus according to the present disclosure.

As shown in FIG. 2, an exemplary individual (primary) detector element 106 according to the present disclosure is shown associated with detector substrate 214 (e.g. a ceramic substrate), and generally comprises a plurality of membranes and/or layers, including e.g., the insulating layer 260, and electrolyte layer 250, an enzymatic gel matrix of the type described above 240, an inner membrane 220, an exterior membrane shell 230, and a non-enzymatic membrane 277. Such membranes and layers are associated with the structure of individual detector elements, although certain membrane layers can be disposed in a continuous fashion across the entire detector array surface or portions thereof that include multiple detectors, such as for economies of scale (e.g., when multiple detectors are fabricated simultaneously), or for maintaining consistency between the individual detector elements by virtue of making their constituent components as identical as possible.

As noted above, the exemplary sensor apparatus 100 includes both primary (enzymatic) and secondary (non-enzymatic) detector elements; while FIG. 2 illustrates one embodiment of the former, the latter is in the exemplary embodiment generally similar in structure, with the exception that the enzymatic matrix 240 is replaced with a non-enzymatic matrix or other structure; i.e., in the case of a glucose-sensitive primary detector, it does not include the glucose oxidase and catalase described elsewhere herein. It will be appreciated, however, that the construction of primary and secondary detector elements need not be substantially similar, and in fact may differ significantly in construction so long as the desired performance attributes are maintained.

The detector element 106 further comprises a working electrode 217 in operative contact by means of electrolyte layer 250 with a counter electrode 219 and a reference electrode 218, and their associated feedthroughs 280 (details of the exemplary feedthroughs 280 are described in U.S. Pat. No. 8,763,245 to Lucisano et al. entitled "Hermetic feedthrough assembly for ceramic body," previously incorporated by reference herein). The working electrode 217 comprises an oxygen-detecting catalytic surface producing a glucose-modulated, oxygen-dependent current (discussed infra), reference electrode 218 comprises an electrochemical potential reference contact to electrolyte layer 250, and counter electrode 219 is operably connected by means of electrolyte layer 250 to the working electrode 217 and reference electrode 218. An electrical potentiostat circuit (not shown) is coupled to the electrodes 217, 218, and 219 to maintain a fixed potential between the working and reference electrode by passing current between the working and counter electrodes while preferably maintaining the reference electrode at high impedance. Such potentiostat circuitry is well known in the art (for an example, see U.S. Pat. No. 4,703,756 to Gough et al. entitled "Complete glucose monitoring system with an implantable, telemetered sensor module," incorporated herein by reference in its entirety).

Generally, the thickness of each of the membranes disclosed herein is not particularly limited, as long as the desired permeability properties are achieved. However, particular requirements for sensor response time, glucose concentration detection range, and/or reduction of antibody response (e.g., FBR), may impose limits on the allowable membrane thickness. Membrane thickness can be, for example, about 1 micron to about 1000 microns, or more particularly, about 10 microns to about 500 microns, or more particularly about 25 microns to about 250 microns, or more particularly about 25 microns to about 75 microns. Very thin membrane layers, particularly those less than about 10 microns, may require mechanical support to be provided in the form of a backing membrane, which may be a porous, relatively inert structure. U.S. Pat. No. 7,336,984 and entitled "Membrane and Electrode Structure for Implantable Sensor," previously incorporated herein, describes exemplary membrane apparatus, thickness values, and computerized modeling techniques useful with the various aspects of the present disclosure, although it will be recognized that other techniques, apparatus, and methods for membrane configuration may be used consistent with the present disclosure.

The electrolyte layer 250 comprises, in the illustrated embodiment, a layer of hydrophilic electrolyte material which is in direct contact with the working electrode(s) 217, reference electrode(s) 218 and counter electrode(s) 219. In various implementations, materials for constructing the hydrophilic electrolyte layer 250 include salt-containing gels comprising polyacrylamide, poly(ethylene oxide) poly (hydroxyethylmethacrylate) and its derivatives, and other hydrophilic polymers and copolymers, in both crosslinked and non-crosslinked form. Various other construction details of the exemplary electrolyte layer 250 are described in U.S. Patent Application Publication No. 2013/0197332 filed Jul. 26, 2012 entitled "Tissue Implantable Sensor With Hermetically Sealed Housing," each incorporated by reference herein in its entirety.

In an exemplary embodiment, the enzymatic material 240 comprises a crosslinked gel of hydrophilic material including enzymes (e.g., glucose oxidase and catalase) immobilized within the gel matrix, including a buffer agent and small quantities of a chemical cross-linking agent. The hydrophilic material 240 is permeable to both a large molecule component (e.g. glucose) and a small molecule component (e.g. oxygen). In various embodiments, specific materials useful for preparing the enzymatic material 240, include, in addition to an enzyme component, polyacrylamide gels, glutaraldehyde-crosslinked collagen or albumin, poly(hydroxyethylmethacrylate) and its derivatives, and other hydrophilic polymers and copolymers, in combination with the desired enzyme or enzymes. The enzymatic material 240 can similarly be constructed by crosslinking glucose oxidase or other enzymes with chemical crosslinking reagents, without incorporating additional polymers.

The enzymatic material 240 is in operative contact with the working electrode 217 through the inner membrane 220 and the electrolyte layer 250 to allow for the electrochemical detection of oxygen at the working electrode 217 modulated by the two-step chemical reaction catalyzed by glucose oxidase and catalase discussed above. To that end, as glucose and ambient oxygen diffuse into the enzymatic material 240, they encounter the resident enzymes (glucose oxidase and catalase) and react therewith; the oxygen that is not consumed in the reaction(s) diffuses through the inner membrane 220 and is detected at the working electrode 217 to yield a glucose-dependent oxygen signal.

A hydrophobic material is utilized for inner membrane 220, which is shown in FIG. 2 as being disposed over the electrolyte layer 250. The hydrophobic material is impermeable to the larger or less soluble molecule component (e.g. glucose) but permeable to the smaller or more soluble molecule component (e.g. oxygen). In various embodiments, materials useful for preparing hydrophobic layers, including inner membrane 220, as well as membrane shell 230, include organosilicon polymers, such as polydimethylsiloxane (PDMS) and derivatives thereof, polymers of tetrafluoroethylene, ethylene tetrafluoroethylene, or fluorochloro analogs alone or as copolymers with ethylene or propylene, polyethylene, polypropylene, cellulose acetate, and other oxygen-permeable polymeric materials.

The inner membrane 220 can also be a continuous layer across the entire detector array surface, and thus be a single common layer utilized by all detectors in the detector array. It is noted that the inner membrane 220, inter alia, protects the working electrode 217, reference electrode 218 and counter electrode 219 from drift in sensitivity due to contact with certain confounding phenomena (e.g. electrode "poisoning"), but the working electrode 217 will nonetheless be arranged sufficiently close to the enzymatic material to enable detection of oxygen levels therein.

The (hydrophobic) outer membrane shell 230 is disposed over at least a portion of the enzymatic material 240 (forming a cavity 271 within which the material 240 is contained), and is further configured to include an aperture within a "spout" region 270 (discussed in greater detail infra). In the exemplary embodiment, the membrane shell 230 is separately provided and adhesively bonded to the inner membrane 220, although it is also contemplated that the inner membrane 220 and the membrane shell 230 can be coextensive and therefore be disposed as one continuous membrane layer in which outer membrane shell 230 and inner membrane 220 are of the same uniform thickness of membrane across the individual detector and array.

As shown in the exemplary embodiment of FIG. 2, inner membrane 220 and membrane shell 230 are disposed in a manner that creates discrete three-dimensional regions having different thicknesses on the detector substrate 214, which can be utilized to create tissue anti-migration elements used to achieve stability of location and prevention of device migration away from its original implant location. Alternatively, the hydrophobic component may be dispersed as small domains in a continuous phase of the hydrophilic material. Various other construction details of the hydrophobic component dispersed as small domains in a continuous phase of hydrophilic material are described in U.S. Pat. Nos. 4,484,987 and 4,890,620, each incorporated herein by reference in its entirety.

The exemplary sensor apparatus is made biocompatible to allow for long term implantation into biological tissue. Thus all membrane structures that are in direct contact with the surrounding biological material are biocompatible and not problematically immunogenic. The membrane materials disclosed herein that are in direct contact with tissue (i.e., the non-enzymatic membrane element 277 and the outer membrane (shell) 230 are generally known to be biocompatible and suitable for long term implantation. However, in some embodiments, all or discrete regions of the sensor may include one or more additional coatings or membrane layers of non-erodible biocompatible material, which may be included to ensure that the immunogenic potential of all exposed materials remains suitably low.

Exemplary Spout Region of the Detector Element

Figure 2A:
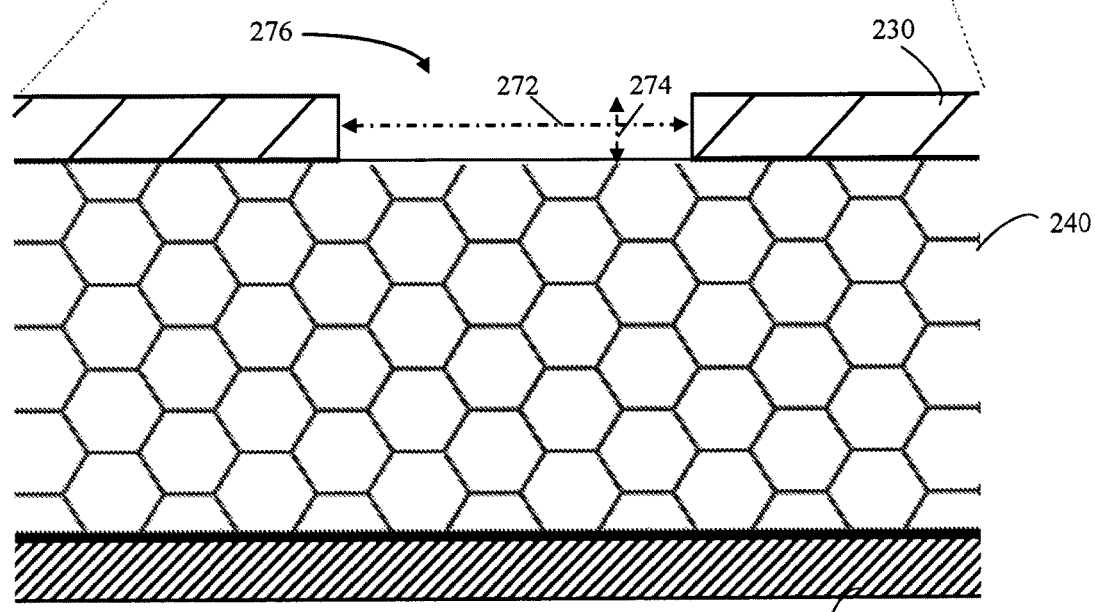
FIG. 2A is a side cross-sectional view of one exemplary spout region (outer non-enzyme membrane removed) of a detector element of a detector array in a fully implantable sensor apparatus according to one embodiment of the present disclosure.

As shown in FIGS. 2-2A, a single spout region 270 of the detector element 106 forms a small opening or aperture 276 through the membrane shell 230 to constrain the available surface area of hydrophilic enzymatic material 240 exposed for diffusionally accepting the solute of interest (e.g. glucose) from solution. Alternatively, it is contemplated that one or more spout regions (and or apertures within a spout region) can exist per detector element.

The shape and dimension of spout region 270 aids in controlling the rate of entry of the solute of interest (e.g. glucose) into enzymatic material 240, and thus impacts the effective operational permeability ratio of the enzymatic material 240. Such permeability ratio can be expressed as the maximum detectable ratio of glucose to oxygen concentration of an enzymatic glucose sensor, where such a sensor is based on the detection of oxygen unconsumed by the enzyme reaction, and after taking into account the effects of external mass transfer conditions and the enzyme reaction stoichiometry. Detailed discussions of the relationship between membrane permeability ratio and the maximum detectable ratio of glucose to oxygen concentration of oxygen-detecting, enzymatic, membrane-based sensors are provided in "Model of a Two-Substrate Enzyme Electrode for Glucose," J. K. Leypoldt and D. A. Gough, *Analytical Chemistry*, 56, 2896 (1984) and "Diffusion and the Limiting Substrate in Two-Substrate Immobilized Enzyme Systems," J. K. Leypoldt and D. A. Gough, *Biotechnology and Bioengineering*, XXIV, 2705 (1982), incorporated herein by reference. The membranes of the exemplary detector element described herein are characterized by a permeability ratio of oxygen to glucose of about 200 to about 1 in units of (mg/dl glucose) per (mmHg oxygen). Note that while this measure of permeability ratio utilizes units of a glucose concentration to an oxygen concentration, it is nevertheless a measure of the ratio of oxygen to glucose permeability of the membrane.

The exemplary spout 270 is formed out of the hydrophobic material of the membrane shell 230 without bonded enzymes (e.g., silicone rubber) and advantageously includes a non-enzymatic outer layer or membrane 277 to, inter alia, prevent direct contact of the immobilized enzymes in the enzymatic material 240 with the surrounding tissue, thereby eliminating and/or reducing antibody response (e.g., FBR), encapsulation, and/or other deleterious factors. In exemplary embodiments, the non-enzymatic membrane 277 is further constructed (i.e., with a substantially planar crosslinked biocompatible matrix possessing pores substantially smaller than those required to accommodate blood vessel ingrowth, but large enough to accommodate diffusion of solutes of interest) so as to frustrate or mitigate blood vessel formation therein. (Suitable pores include those with an effective diameter ranging from approximately 10 angstroms up to approximately 10 microns.) Herein lies a salient feature of the sensor element of the exemplary embodiment; i.e., the combination of (i) an enzyme-free biocompatible outer membrane 277, (ii) maintenance of the spout region substantially free of enzyme material during manufacture (see discussion of manufacturing methods below), (iii) use of a non-porous crosslinked structure for the membrane 277, and (iv) use of a biocompatible material (e.g., silicone rubber) for the outer membrane shell 230, dramatically reduces the level of FBR of the host while the device is implanted, thereby allowing for both longer implantation (due to, inter alia, the reduced level of FBR not interfering with sensor operation) and easier explants of the device, as compared to e.g., peroxide-based sensors without such features. The inner hydrophobic membrane 220 further provides additional insulation of the host tissue in the region of the detector 106 against any electrical potentials which may be present with in the sensor element, thereby further aiding in mitigating FBR. In various implementations, materials for constructing the membrane layer 277 include gels comprising proteins such as albumin and collagen, as well as non-proteinaceous polymers such as polyacrylamide, poly (ethylene oxide) poly(hydroxyethylmethacrylate) and its derivatives, and other hydrophilic polymers and copolymers, in both crosslinked and non-crosslinked form.

The spout aperture diameter 272 in part controls the effective operational membrane permeability ratio. In the exemplary embodiment, the aperture diameter is correlated to the range of concentration the target analyte (e.g., glucose) that can be detected by the detector element. A larger aperture diameter corresponds to a lower permeability ratio of oxygen to glucose, and hence a greater sensitivity to a given concentration of glucose within the tissue proximate the aperture (and therefore a lower minimum concentration that can be accurately detected). However, with the larger aperture, the detector will "saturate" more rapidly at a given oxygen concentration, and hence the upper bound of detection is similarly reduced. Conversely, a smaller diameter aperture corresponds to an increased permeability ratio, and hence a higher minimum effective sensitivity (and corresponding higher maximum detectable concentration before saturation is reached).

Figure 2B:
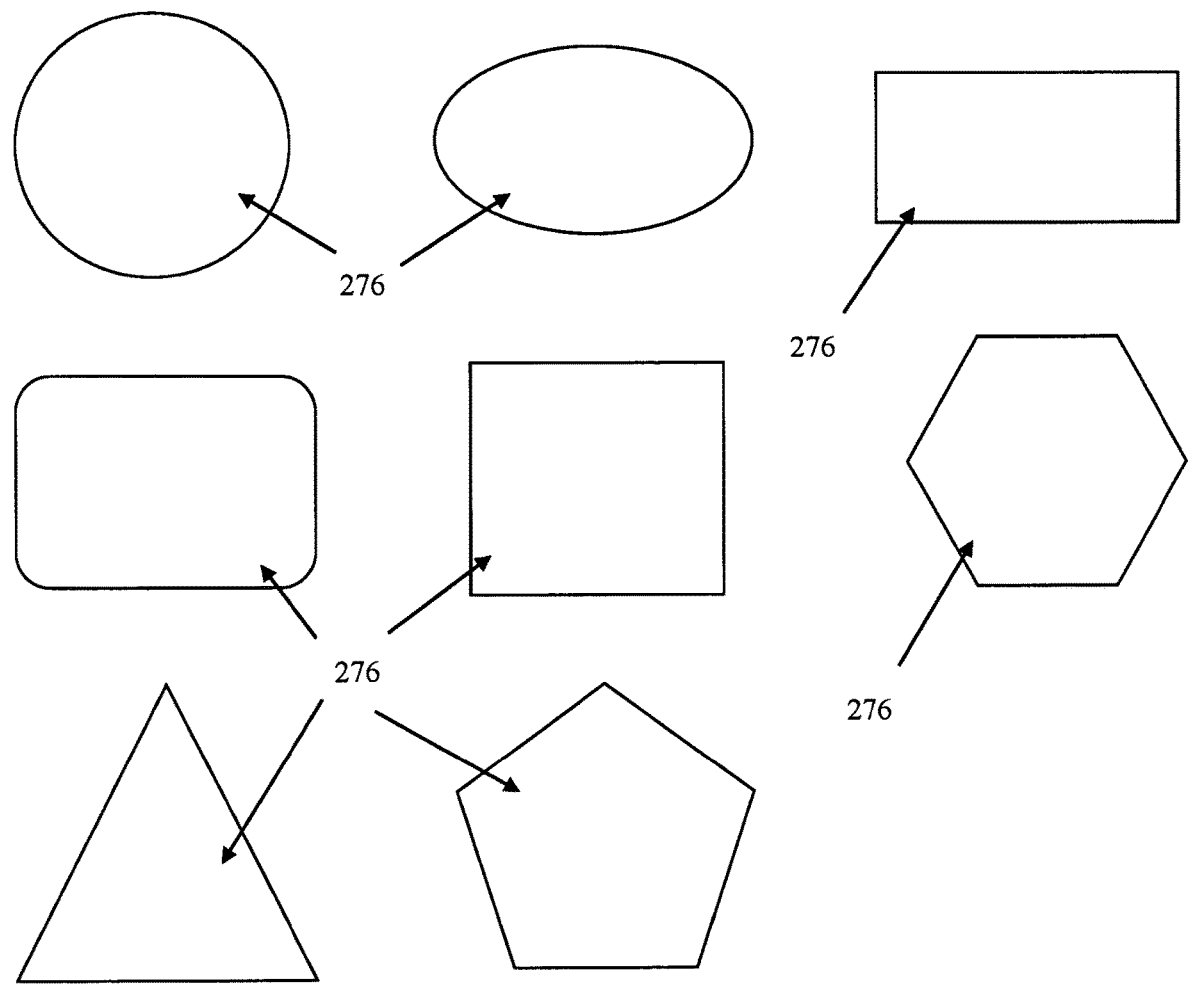
FIG. 2B is a graphical representation of top elevation views of a variety of different exemplary embodiments of sensor membrane apertures according to the present disclosure.

It is also appreciated that the (i) in various embodiments, the aperture 276 of the spout region 270 may be virtually any geometric shape so long as the desired permeability ratio is achieved, such as, for example, round, oval, elliptical, rectangular, triangular, star shaped, square, polygonal, and the like (see FIG. 2B), or even irregular, although round (circular) apertures are generally preferred because such shapes are more amenable to manufacturing; and (ii) diameter is straightforwardly related to area, and the present disclosure contemplates that area may be a useful measure of "spout size" as it relates to adjusting the operational characteristics of the detector element in place of diameter.

Moreover, other dimensional parameters have been identified by the inventors hereof as having an impact on detector element performance, and being a means by which such performance can be adjusted or optimized as desired. For example, in addition to diameter of the aperture 276, the placement of the aperture(s) relative to the base of the cavity (e.g., height of the aperture above the base), the height 275 of the base region above the underlying inner membrane (see FIG. 2), and even the vertical height of the sidewalls of the aperture itself 274 (see FIG. 2A) can significantly affect the operation of the detector, including especially its response rate or detection time. See, e.g., U.S. Pat. No. 7,336,984 and entitled "Membrane and Electrode Structure for Implantable Sensor," previously incorporated herein, which describes exemplary values (and techniques of determining such values) for an implantable glucose sensor of the type described herein.

Similarly, the diameter 273 of the base region (i.e., that region underlying the outer membrane 230; see FIG. 2) can affect operation of the detector, including specifically the range of concentrations of analyte that can be measured.

Hence, the present disclosure contemplates use of one or more of the foregoing dimensional parameters to configure or optimize the operation of the detector element 106 for a prescribed application.

Figure 3:
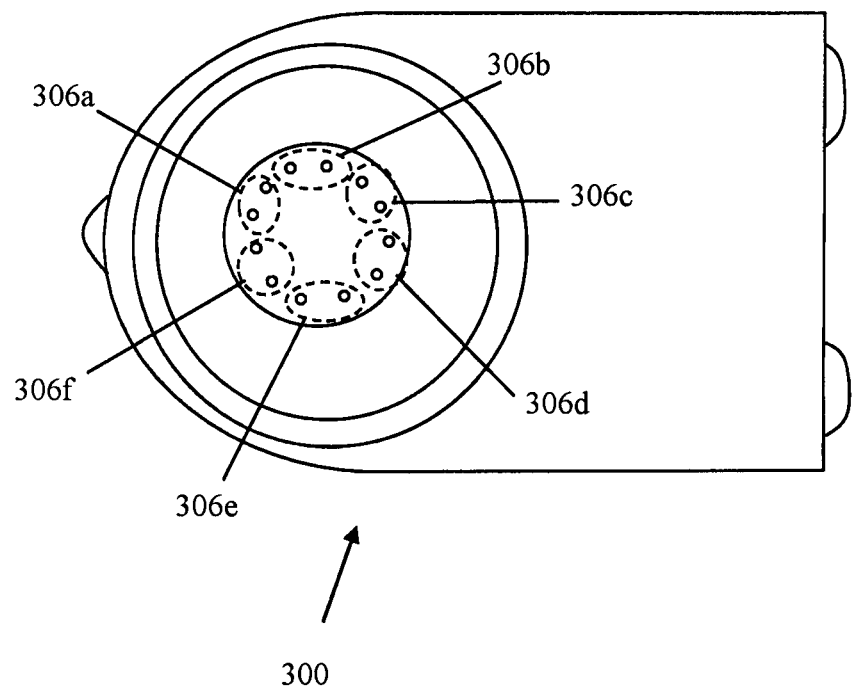
FIG. 3 is a top elevation view of another exemplary embodiment of the sensor apparatus of present disclosure, wherein multiple sensor/reference pairs with at least partly differing glucose sensing ranges are used on a common device.

As will be apparent to those skilled in the art, the outer (non-enzymatic) membrane layer 277 can be formed in any number of different ways. In the exemplary embodiment (see discussion of FIG. 3 below), the non-enzymatic layer 277 is in effect "pour filled" into the aperture 276 of the outer housing membrane 230 atop the (crosslinked) enzymatic membrane matrix 240. However, the present disclosure contemplates other techniques for formation, including for example provision of a pre-formed membrane 277 which is inserted into the aperture in operative contact with the enzyme material 240, or even chemical or other treatments of the upper surface of enzyme material 240, including various de-immunizing treatments. In all cases, it is required that the outer membrane layer 277 be sufficiently permeable to analytes and co-reactants to enable correct operation of the detector. In the exemplary embodiment, the outer membrane 277 comprises a crosslinked albumin, which exhibits the aforementioned desirable properties of (i) lack of FBR-inducing enzymes, (ii) non-porosity, and (iii) electrical insulation. Notably, the exemplary albumin material used for the membrane layer 277 is biocompatible; in the present context (a tissue-located implant), the term 'biocompatible' as applied to the membrane layer 277 indicates that the material itself does not significantly exacerbate the FBR which is otherwise expected to occur with any implant. So, the amount/degree of fibrous tissue formation that results from the FBR (which nonetheless occurs due to natural body processes) is advantageously minimized, compared to what might be obtained with another less-biocompatible material.

Notably, in the exemplary implementation, the hydrophilic albumin of the outer membrane 277 is in direct contact with the (hydrophilic) tissue of the host, thereby advantageously providing a "like-to-like" interface, which also contributes to the stability of the detector elements over time due to, among other things, the aforementioned non-exacerbation of FBR or other host responses.

It is also noted that the exemplary membrane layer 277 described herein, by virtue of its non-exacerbation of FBR in the host (e.g., through use of a biocompatible material such as crosslinked albumin), further results in mitigation of the formation of significant fibrous tissue response, which could otherwise interfere with optimal operation of the sensor detector elements or reduce their accuracy due to, inter alia, reduced blood vessel density in the fibrous tissue. So, in effect, the non-exacerbation of FBR and non-encouragement of blood vessel ingrowth into the membrane layer 277 by the exemplary embodiment herein actually (and somewhat counter-intuitively) stabilizes blood perfusion and blood glucose delivery to the detector elements, and avoids having to second-guess the largely unpredictable modulation process, especially over longer periods of implantation.

Other biostable polymers suitable as outer (housing) membrane materials include, for example, hydrophilic polyurethanes, silicones, poly(hydroxyethylmethacrylate)s, polyesters, polyalkyl oxides (polyethylene oxide), polyvinyl alcohols, and polyethylene glycols and polyvinyl pyrrolidone. See, inter alia, U.S. Patent Application Publication No. 2013/0197332 previously incorporated herein, for a discussion of other various outer membrane materials.

Figure 2C:
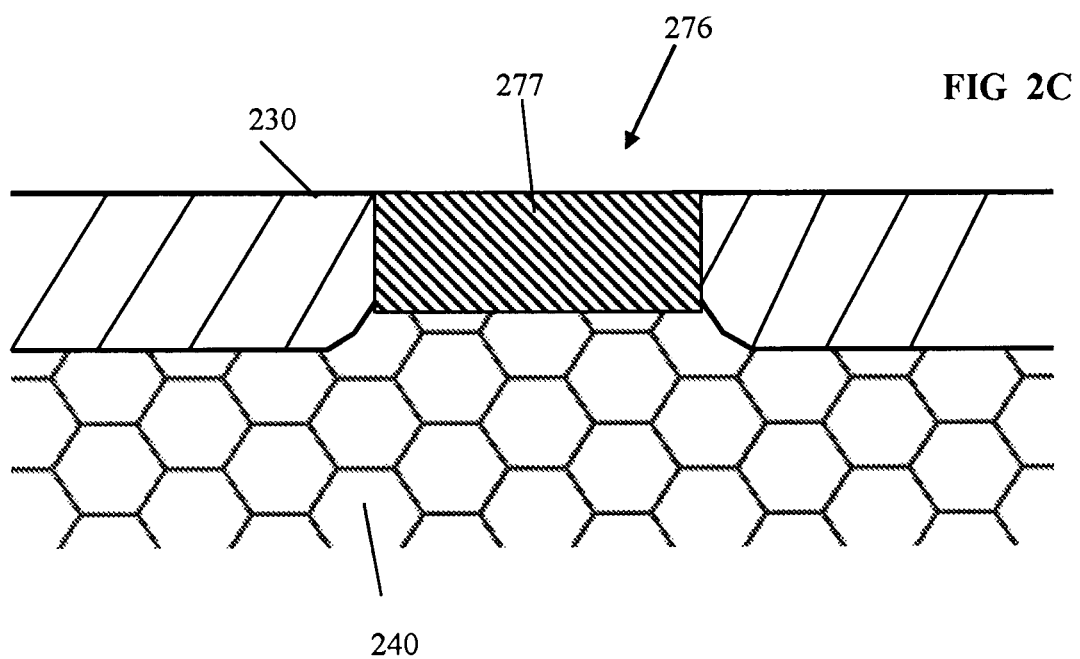
FIGS. 2C-2F are side cross-sectional views of respective ones of a variety of different exemplary embodiments of sensor membrane apertures according to the present disclosure.
Figure 2D:
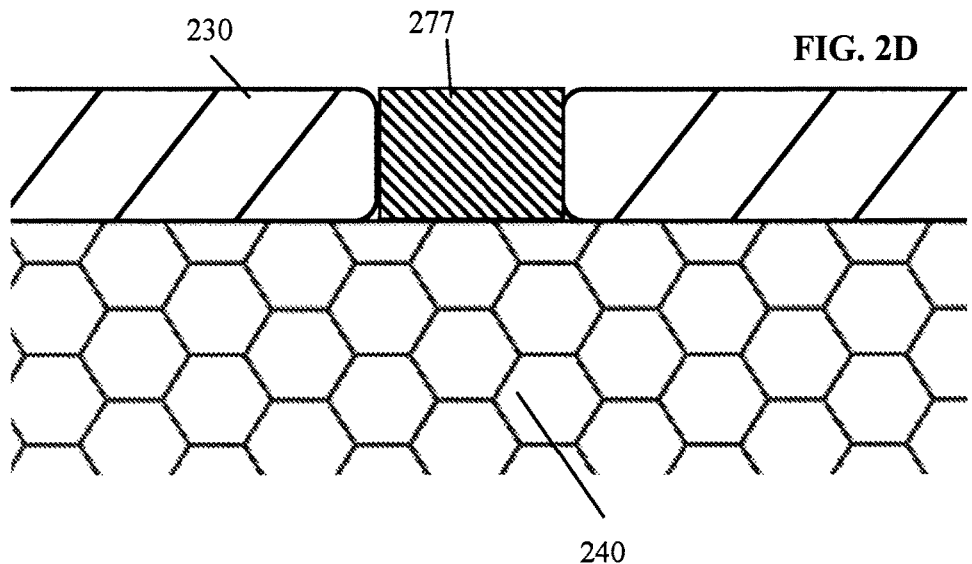

It will also be appreciated that the "vertical" spout/aperture profile can take on many forms as dictated by a given application. See e.g., FIGS. 2C-2F, wherein several exemplary configurations (shown in cross-section) of apertures and enzyme material 240 are shown. As will be appreciated by those of ordinary skill given this disclosure, the configuration of the aperture, including its placement relative to other components within the detector element (including outer membrane 230, inner membrane 220, etc.), can affect the operation of the detector element. For example, the present disclosure contemplates that a rounded or smoothed and progressively narrowing aperture/spout shape (see FIG. 2C) as one embodiment.

Figure 2E:
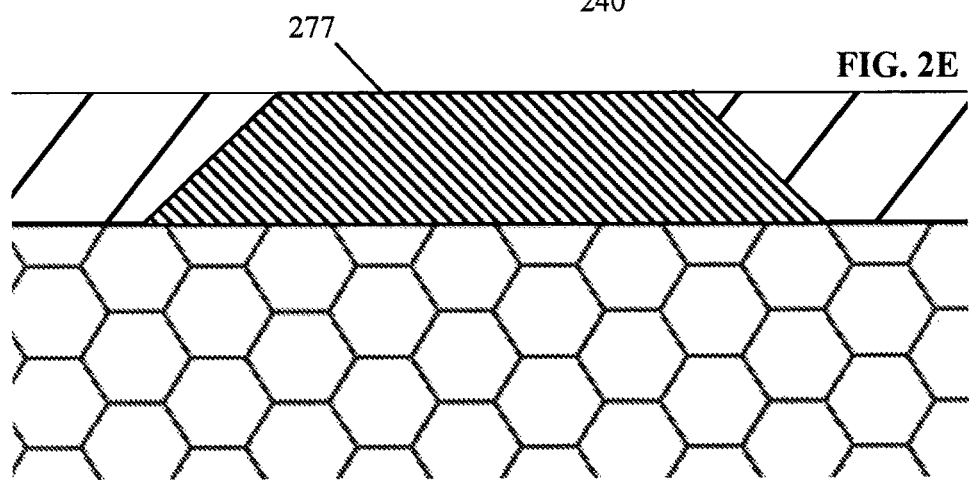
Figure 2F:
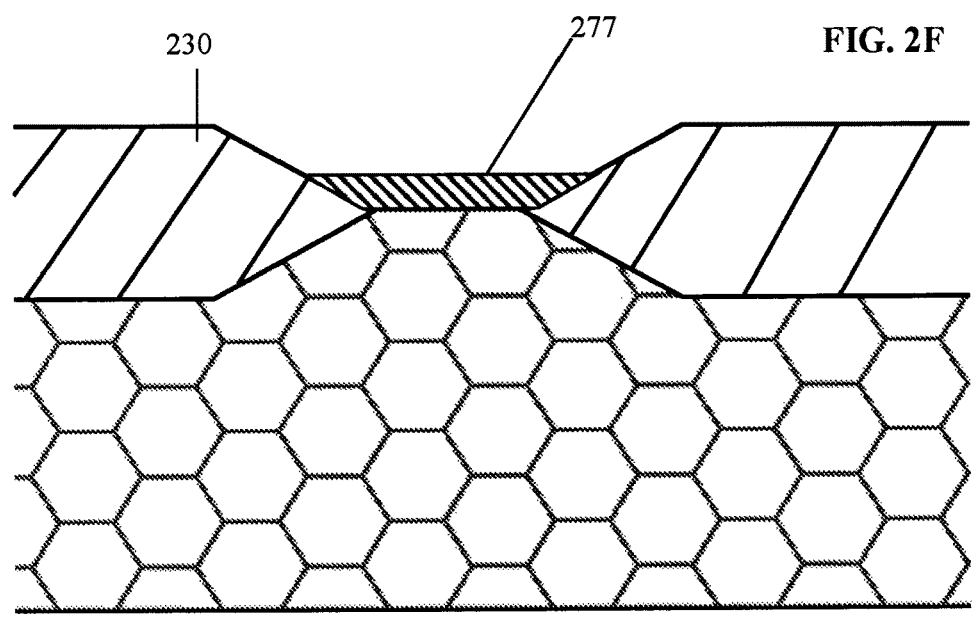

Likewise, a tapered or chamfered aperture (either "taper up" or "taper down," or both; see FIGS. 2E and 2F) may be useful in certain circumstances. Notably, the "taper up" embodiment of FIG. 2E provides an added advantage relating to mechanical stability; i.e., the taper of the non-enzymatic membrane 277 and sidewalls of the aperture 276 cooperate to retain the membrane 277 (once cured) in place, and resist dislocation or movement potentially resulting from e.g., thermal expansion of the underlying enzyme matrix 240, or interaction between the outer surface of the membrane 277 and the host tissue/encapsulation FBR which might tend to draw the membrane 277 out of the aperture 276. It will be appreciated that other shapes may similarly be used to provide such mechanical stability, such as e.g., an inverted "T" shape (not shown).

As yet another example, a "rounded edge" or bull-nosed configuration of the aperture (FIG. 2D) may be useful.

Yet other configurations will be recognized by such skilled artisans when given the disclosure. These various vertical aperture/spout profiles may further be combined with one or more of the "horizontal" planar aperture shapes shown in FIG. 2B (or yet others) in order to achieve the desired performance attributes. It will also be appreciated that the thickness of the non-enzyme layer or membrane 277 may also be varied (as can other properties of the non-enzymatic membrane 277, such as density or permeability) so as to effect the desired rate of permeation of the analyte and any associated coreactant(s) (e.g., glucose and oxygen) through the membrane, and also to frustrate or control blood vessel growth into the membrane 277.

Yet further, it is recognized that the membrane 277 need not have a consistent shape or thickness; e.g., it may have thicker or narrower regions (which may or may not be symmetrical), such as to create regions of e.g., greater or lesser permeation relative to the underlying enzyme-containing matrix 240. In one such variant, the edges of the membrane 277 are made thinner than the central portion, such that more analyte/oxygen permeates through the outer regions per unit time, and hence diffuses to the outer regions of the matrix 240 (i.e., those which are not directly under or proximate to the aperture 276). Hence, a more "even burn" of enzyme material is achieved.

Likewise, it will be appreciated that the "fill level" of enzyme material 240 relative to the spout/aperture can be varied. For example, as shown in the embodiment of FIG. 2A, the top of such enzymatic material 240 is roughly coincident with the height of the bottom of the aperture 276. The foregoing variation in fill level must, however, be consistent with the requirement that at least a portion of the outer (non-enzyme) layer or membrane 277 generally must be in physical or chemical "contact" with the underlying enzyme material 240 (absent any interposed material or vehicle) so as to permit permeation of the analyte(s) (e.g., glucose, and free oxygen) into the enzyme material 240. It will be recognized that such "chemical contact" may take various forms, including direct physical contact, indirect contact via an interposed layer of material or fluid (such as to promote binding of the outer membrane 277 to the matrix 240) which does not substantially mitigate permeation, or yet other ways.

In another variant, the outer membrane 277 may be directly bonded or attached to the underlying matrix (whether enzymatic, such as in the primary detector elements, or non-enzymatic, such as in the secondary detector elements). For example, in one implementation, crosslinked albumin is used in the outer membrane 277, and is bonded to the underlying crosslinked albumin-containing enzymatic matrix 240, so as to promote inter alia, constant and complete glucose and oxygen molecule migration during operation. Further, the direct bonding of the two cited membrane layers helps to ensure a stable mechanical structure of the membrane assembly, a prerequisite in ensuring stable, predictable sensor response characteristics. In one such implementation, the two layers (outer membrane 277 and matrix 240) are bonded via a chemical crosslinking agent such as glutaraldehyde, which, for example, when the layers comprise proteinaceous materials, promotes chemical bonding between the layers as well as crosslinking within each layer.

Moreover, as previously indicated, the outer membrane layer 277 may also be (chemically) bonded to the outer silicone membrane shell 230 such as at the interface between the outer edge of the membrane layer 277 and the inner periphery of the aperture 276. This approach can help further protect against any migration of the enzymes in the matrix 240 outward toward the host tissue, thereby avoiding any exposure thereof (and possible further FBR to the enzyme(s)).

Additionally, it will be appreciated that while in various embodiments, the exemplary spout region 270 is filled or layered with an additional non-enzyme material or membrane 277 (such as to reduce the immunogenic potential of the enzymatic material 240), such layer or membrane 277 may not be required in certain cases. For instance, where a given detector does not utilize any enzymatic material (or uses an enzymatic material that produces limited if any FBR in the host tissue, it may be feasible to eliminate the outer non-enzymatic layer). Moreover, where the spout aperture(s) 276 has a comparatively small diameter, such as where a plurality of small apertures 276 are used in place of a single larger aperture, direct contact surface area with host tissue may be quite small and spatially distributed, thereby potentially obviating the need for the "buffer" membrane 277.

It is also envisioned that a spatial gradient in enzyme concentration within the enzyme material can be employed, such that e.g., the concentration is reduced proximate the host solid tissue, thereby ostensibly mitigating FBR due to irritation by the enzymes, transient peroxides, etc. Further, it is contemplated that a chemical treatment applied during manufacturing could be employed to "de-immunize" an exposed surface of membrane material 240, obviating the need for the buffer membrane 277.

Heterogeneous Detector Element Arrays

It is contemplated that in other embodiments, the detector array 104 includes detector elements 106 with different spout (aperture) diameters and/or other physical characteristics; e.g., one detector or set of detectors with larger spout diameters and/or heights, and another detector/set with smaller spout diameters and/or heights. Having multiple detector elements 106 with such different physical characteristics (and hence operating characteristics) is beneficial for any number of reasons, including maintaining a broader desired sensor response range.

For example, where the variation of the concentration of the underlying analyte being measured is substantial (whether spatially or over time), there is the possibility that a detector or set of detectors with e.g., a common, finite range of detection may be "over-ranged" or "under-ranged" such that it/they are incapable of accurately detecting the concentration through such a broad range of levels.

In one implementation (see FIG. 3), twelve (12) sensor elements are included on the sensor apparatus 300, two (2) of which 306a are configured to measure glucose level within a first response range, two of which 306c are configured to measure glucose level within a second (at least partly differing) response range, and two of which 306e are configured to measure glucose level within a third range which is at least partly different from the first and second ranges. The remaining six (6) sensor elements 306b, 306d, 306f are used to measure oxygen concentration (i.e., are reference elements).

Moreover, it will be appreciated that most any sensor will tend to have a detection "sweet spot," wherein the operation of the sensor(s) (e.g., its signal-to-noise ratio and therefore its accuracy) are optimized as compared to operation at other values, such as those at the ends of its dynamic range. Hence, it may be desirable to use that particular detector for measuring analyte concentrations that fall at or near the sweet spot, so as to provide the most accurate results. Having two or more heterogeneous detector elements with differing or staggered sweet spots (such as the apparatus 300 of FIG. 3) thereby enables more accurate measurement over a broader range than if a single detector (range) was used.

Accordingly, another exemplary embodiment of the sensor apparatus described herein may include either or both of: (i) multiple detector elements with respective "staggered" ranges/rates of detection operating in parallel (as in the apparatus of FIG. 3), and/or (ii) multiple detector elements with respective "staggered" ranges/rates of detection that are selectively switched on/off in response to, e.g., the analyte concentration reaching a prescribed upper or lower threshold.

In one such embodiment, the sensor apparatus 300 includes two or more sets of detector elements 306 having different ranges of detection, and associated control logic such that the output of the various detector elements can be selectively utilized while the apparatus 300 is implanted in vivo. In one such approach, each detector element includes a pre-designated upper and lower threshold value for analyte concentration sensitivity, such that operation of the particular detector element outside of those bounds is less desirable (or even inoperable). In one implementation, the detector physical attributes (e.g., aperture diameter, base height, etc.) described above for each successive detector are coordinated such that the upper and lower bounds of each are generally contiguous, thereby forming a "stitched together" virtual sensor with expanded range of detection. The supporting circuitry of the sensor apparatus (or alternatively, off-sensor logic such as on a user's wireless monitor) is configured in one variant to: (i) determine a trend or slope of analyte concentration, and (ii) a proximity to a given threshold for a given detector element (or set of elements), such that the circuitry can "hand off" from one detector element/set (e.g., with a first operational range or sensitivity) to a second element/set with a contiguous or overlapping range or sensitivity), thereby extending the dynamic range of the device as a whole.

Moreover, the aforementioned upper/lower thresholds or bounds can be selected such that the aforementioned "sweet spot" of the particular detector element is primarily used, with handoff to another element/set occurring before significant degradation of performance occurs. Hence, in one scenario, the upper and lower thresholds of a first sensor apparatus 300 with say six (6) heterogeneous, staggered sets of working and reference detectors can be adjusted to "stitch together" the same dynamic range of a similar homogenous detector sensor apparatus (i.e., four sets of identical detector elements, such as the apparatus 100 of FIG. 1), yet with increased accuracy throughout the range, since each of the constituent detector elements in the heterogeneous apparatus 300 are each operating only in their "sweet spot" before handing off to the next detector element.

The present disclosure further contemplates that such thresholds or bounds: (i) can be selected independent of one another; and/or (ii) can be set dynamically while the apparatus 300 is implanted. For example, in one scenario, operational detector elements are continuously or periodically monitored to confirm accuracy, and/or detect any degradation of performance (e.g., due to equipment degradation, progressive FBR affecting that detector element, etc.); when such degradation is detected, affecting say a lower limit of analyte concentration that can be detected, that particular detector element can have its lower threshold adjusted upward, such that handoff to another element capable of more accurately monitoring concentrations in that range.

Alternatively, each of the aforementioned heterogeneous sensor sets 306a-f may simply be operated in parallel, and data generated by each transmitted off-device (e.g., via wireless interface to an external receiver) for subsequent processing of the raw data on the external receiver device or on an external computational platform, such as via application software running on a personal computer or server and configured to identify the most optimal data from each sensor set 306 within the "raw" data generated by that sensor set and transmitted off-device, and utilize the identified optimal data to provide a representation of the measured analyte concentration over the entire range of values encountered, ostensibly with greater accuracy than that provided by a comparable homogenous detector configuration. For instance, in one such implementation, the sensor sets 306 are evaluated at e.g., time of manufacture (or statistically modeled) so that the "sweet spot" of each particular set on a given device 300 is known a priori; such evaluation or modeling data is utilized by the aforementioned application software to filter data obtained from the in situ device 300 so as to retain only data associated with measured glucose concentrations falling within the optimal range of each particular sensor set 306.

Methods for Manufacturing

Figure 4:
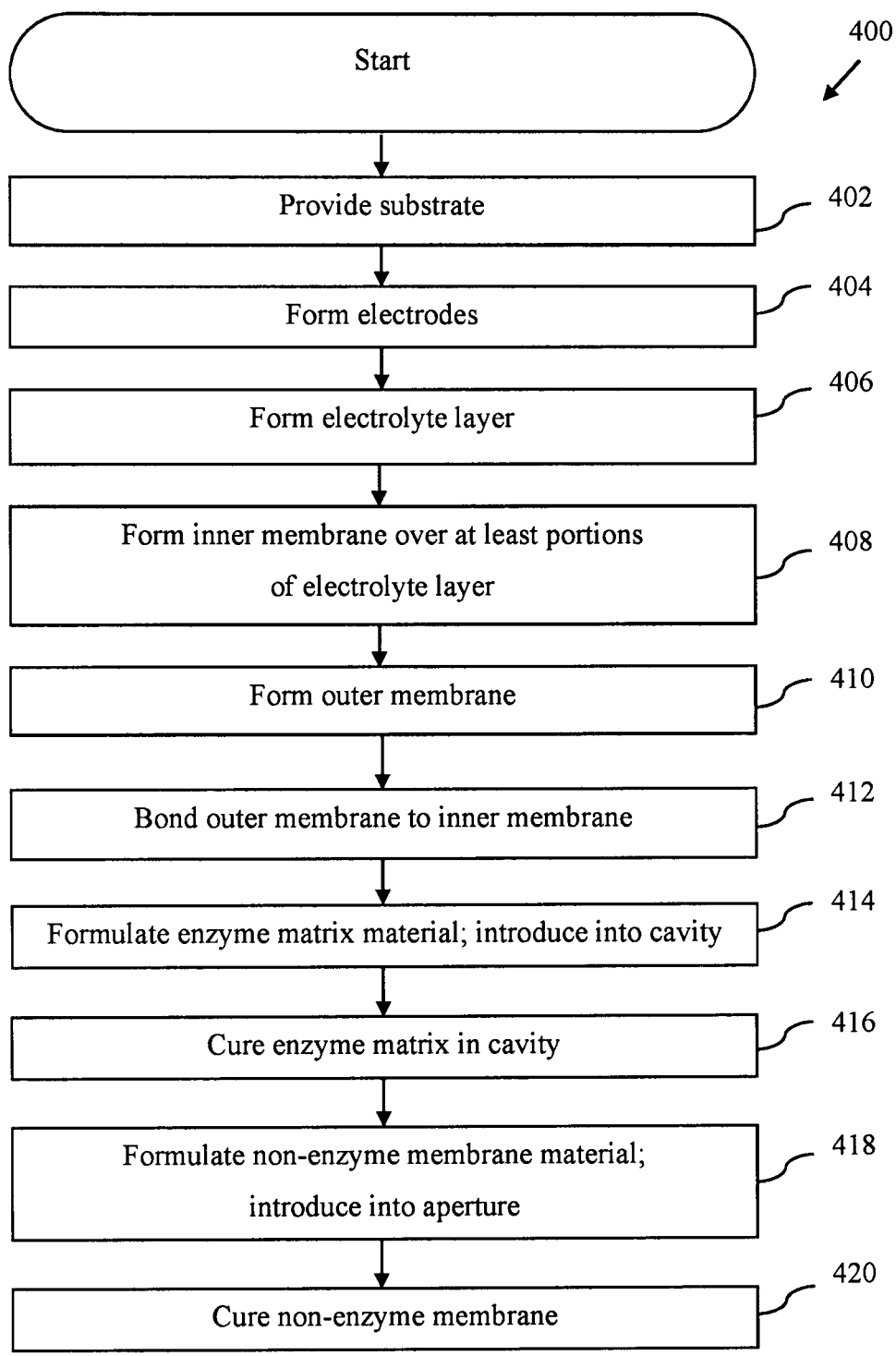
FIG. 4 is a logical flow diagram of one embodiment of a method of manufacturing a sensor element according to the present disclosure.

In another aspect, methods of manufacturing one or more sensor apparatus 100, 300 of the present disclosure are described in detail. Referring now to FIG. 4, one exemplary embodiment of a method 400 of manufacturing the various membranes and/or layers of the exemplary detector element including the novel spout region is disclosed.

In the illustrated embodiment, the method 400 includes first providing a substrate (e.g. ceramic or similar) per step 402. Next, the working, reference and counter electrodes (as applicable) 217, 218, 219 and associated feedthroughs are formed within the substrate (in one embodiment as previously described herein with reference to U.S. Pat. No. 8,763,245 to Lucisano et al. entitled "Hermetic feedthrough assembly for ceramic body") per step 304.

Next, per step 406, an electrolyte layer is formed over at least a portion of the substrate, including at least a portion of the electrodes.

An inner (e.g., polymer, oxygen-permeable) membrane 220 is next formed over the electrolyte layer per step 408. In one embodiment, the inner membrane comprises a silicone rubber compound, although it will be appreciated that other materials may be used consistent with the present disclosure.

Per step 410, the outer hydrophobic membrane 230 is next formed (although this can also be formed concurrently with the inner membrane), such as via molding of a silicone rubber compound identical or similar to that used for the inner membrane in the desired shape and dimensions, including the aperture 276. Advantageously, the mold(s) used for forming the outer membrane 230 can easily be modified or adjusted (or multiple molds used), such that detectors with different operating characteristics can readily be produced (including variants where all other components remain the same).

The outer membrane 230 is formed or disposed over the inner membrane per step 412 such that the inner and outer membranes form a cavity to encapsulate the enzyme material 240. In the exemplary embodiment, the inner membrane 220 and outer membrane 230 are joined together via an adhesive (e.g., room temperature vulcanizing (RTV) rubber adhesive) or other bonding process, although it is also appreciated that the outer hydrophobic membrane and the inner membrane may potentially be formed as a common component (i.e., one piece) when the materials selected for each are the same.

Next, per step 414, the enzyme matrix material 240 is formulated and inserted into the cavity 271 such that it at least contacts the inner membrane and aperture (i.e., to the desired level), and then cured (e.g., via the introduction of added chemical cross-linking agent) to effectuate the desired degree of crosslinking (and enzyme immobilization). In the exemplary embodiment, the enzyme matrix material 240 includes the enzyme components (i.e., catalase, oxidase), as well as a binder protein (albumin), all dissolved in an aqueous buffer (phosphate-buffered saline), and also a small percentage by volume of a chemical cross-linking agent such as glutaraldehyde. The resulting mixture is in a substantially liquid or flowable form before introduction into the cavity formed between the inner and outer membranes 220, 230. Advantageously, use of the buffer and the cross-linking agent within the liquid/flowable enzyme material mixture helps reduce or eliminate formation of voids or "bubbles" within the material after curing (discussed below), thereby enhancing the performance of the sensor element after implantation.

Moreover, in certain embodiments, it is desired to maintain at least portions of the side surfaces of the aperture 276 substantially enzyme-free, so as to inter alia, mitigate the chances of any enzyme material coming in contact with the host's surrounding tissue (i.e., after implantation), such contact potentially resulting in undesired FBR due to exposure to the enzymes. Hence, in one implementation, the enzyme material mixture 240 is used to fill the cavity 271 up to a level coincident with the bottom edge of the side walls of the aperture 276, and the enzyme material is prevented from contacting the sidewalls during such fill.

Next, per step 416, the enzyme material 240 within the cavity 271 is "cured," such as via the application of additional chemical cross-linking agent atop the material 240 via the aperture 276, or by diffusion through the outer membrane 230. It will be appreciated, however, that while chemical cross-linking is described herein with respect to the exemplary embodiments, the disclosure contemplates other means of curing the matrix material, including e.g., via heat and/or radiation, whether alone or in combination with the aforementioned chemical agents.

After the curing (e.g., crosslinking) of the enzyme matrix material is completed, the non-enzyme membrane material is formulated and introduced into the aperture region 276 (step 418). In the exemplary embodiment, the non-enzyme membrane material is also in a substantially liquefied or flowable form and includes a protein such as an albumin (e.g., recombinant human albumin), and a portion of the aforementioned buffering agent (although different/heterogeneous buffering agents may be used in the enzymatic and non-enzymatic membranes if desired). Addition of the cross-linking agent prior to the filling procedure has not been found advantageous with the albumin material, therefore its inclusion prior to filling is not required.

Once the non-enzyme membrane material is disposed within the aperture to the desired height (e.g., approximately even with the top surface of the outer membrane 230 proximate the aperture 276), the non-enzyme material is cured (e.g., via chemical cross-linking similar to that used for the enzymatic material, or other processes) per step 420. This process further causes bonding between the bottom portion of the non-enzymatic membrane later and the top of the (previously cured) enzymatic material 240 at least in the region of the aperture 276. Advantageously, such bonding helps both avoid the formation of gaps or voids between the layers, and ensures consistent oxygen and glucose migration from the non-enzymatic membrane to the enzyme material during operation.

It will be recognized that while certain embodiments of the present disclosure are described in terms of a specific sequence of steps of a method, these descriptions are only illustrative of the broader methods described herein, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure and claimed herein.

While the above detailed description has shown, described, and pointed out novel features as applied to various embodiments, it will be understood that various omissions, substitutions, and changes in the form and details of the device or process illustrated may be made by those skilled in the art without departing from principles described herein. The foregoing description is of the best mode presently contemplated. This description is in no way meant to be limiting, but rather should be taken as illustrative of the general principles described herein. The scope of the disclosure should be determined with reference to the claims.

What is claimed is:

1. A sensor apparatus, comprising:
a substrate;
signal processing circuitry; and
at least one first detector element and at least one second detector element each in signal communication with the signal processing circuitry, each of the at least one first detector element and the at least one second detector element comprising:
a three-dimensional membrane structure comprising (i) an at least partly enclosed cavity, the at least partly enclosed cavity comprising an enzymatic substance disposed therein, (ii) and at least one spout in communication with the at least partly enclosed cavity;
an electrolyte layer;
one or more electrodes comprising at least a working electrode, a counter electrode, and a reference electrode, an active face of the working electrode, an active face of the counter electrode, and an active face of the reference electrode disposed on an exterior surface of the substrate and at least partly within or contacting said electrolyte layer; and
a non-enzymatic membrane disposed within the at least one spout and at least partly occluding the at least one spout, said non-enzymatic membrane comprising a non-enzymatic material at least partly permeable to an analyte;
wherein the three-dimensional membrane structure is arranged over the exterior surface of the substrate such that (i) the at least partly enclosed cavity is disposed over at least a portion of the active face of the working electrode, and (ii) the at least partly enclosed cavity is offset from the active face of the counter electrode and the active face the reference electrode;
wherein said at least one first detector element is configured to: (i) have a first response characteristic, and (ii) utilize chemical interaction between at least the analyte and the enzymatic substance to enable generation of a first electrical signal at said at least one electrode of the at least one first detector element, said first electrical signal relating to a blood analyte concentration;
wherein said at least one second detector element is configured to: (i) have a second response characteristic at least partially different from the first response characteristic, and (ii) utilize chemical interaction between at least the analyte and the enzymatic substance to enable generation of a second electrical signal at the at least one electrode of the at least one second detector element, the second electrical signal relating to the blood analyte concentration; and
wherein the first response characteristic and the second response characteristic are each based at least on a combination of a cross-sectional area of the at least one spout and a fill-level of the non-enzymatic material within the at least one spout being different for the at least one first detector element relative to the at least one second detector element.

2. The sensor apparatus of claim 1, wherein:
the at least one spout of the at least one first detector element is at least mostly enzyme-free and sized to have at least a first cross-sectional area, the first response characteristic based at least on the first cross-sectional area, the first response characteristic configured to enable the first detector element to determine the blood analyte concentration within a first specified range; and
the at least one spout of the at least one second detector element is sized to have at least a second cross-sectional area different from the first cross-sectional area, the second response characteristic based at least on the second cross-sectional area, the second response characteristic configured to enable the second detector element to determine the blood analyte concentration within a second specified range, the second specified range at least partially non-overlapping with the first specified range.

3. The sensor apparatus of claim 2, wherein the sensor apparatus is configured for complete implantation within a living host, and the reference electrode is configured to provide a reference signal, said reference signal useful in determining the blood analyte concentration.

4. The sensor apparatus of claim 3, wherein the at least one reference electrode comprises an oxygen detector, and said chemical interaction between the analyte and the enzymatic substance for each of the at least one first detector element and the at least one second detector element comprises an oxygen-consuming reaction, each of said first electrical signal and the second electrical signal relating at least in part to an unconsumed portion of oxygen which diffuses into said at least partly enclosed cavity via said non-enzymatic membrane in each of the at least one first detector element and the at least one second detector element.

5. The sensor apparatus of claim 1, wherein:
the at least one spout is formed and the non-enzymatic membrane is disposed within the at least one spout so that, between a bottom surface of the cavity and a bottom surface of the non-enzymatic membrane, the at least partly enclosed cavity respectively comprises a first height for the at least one first detector element and a second height for the at least one second detector element;
the first response characteristic is further based on the first height, the first response characteristic configured to enable the first detector element to determine the blood analyte concentration within a first specified period of time of the analyte being introduced into a region external to the at least partly enclosed cavity of the at least one first detector element; and
the second response characteristic is further based on the second height, the second response characteristic configured to enable the second detector element to determine the blood analyte concentration within a second specified period of time of the analyte being introduced into a region external to the at least partly enclosed cavity of the at least one second detector element, the second specified time period at least partially non-overlapping with the first specified time period.

6. The sensor apparatus of claim 1, wherein:
the at least one spout of the at least one first detector element comprises a first shape, the first response characteristic further based on the first shape; and
the at least one spout of the at least one second detector element comprises a second shape different in at least one dimension from the first shape, the second response characteristic further based on the second shape.

7. The sensor apparatus of claim 6, wherein the first shape comprises at least one first curved interior surface in communication with the at least partly enclosed cavity of the at least one first detector element, and the second shape comprises at least one second curved interior surface in communication with the at least partly enclosed cavity of the at least one second detector element, the at least one second curved interior surface having a different degree of curvature relative to the at least one first curved interior surface.

8. The sensor apparatus of claim 1, wherein the non-enzymatic membrane comprises a crosslinked albumin-based compound, and the three-dimensional membrane structure comprises a hydrophobic material having the at least partly enclosed cavity formed therein, the hydrophobic material in communication with at least a portion of the non-enzymatic membrane so as to seal the at least one spout.

9. The sensor apparatus of claim 8, wherein the three-dimensional membrane structure further comprises a permeable layer in communication with at least a portion of the enzymatic substance and at least a portion of the electrolyte layer, the permeable layer permeable to oxygen.

10. The sensor apparatus of claim 9, wherein the enzymatic substance comprises a hydrophilic material having catalase and glucose oxidase co-immobilized therein.

11. The sensor apparatus of claim 10, wherein the chemical interaction at each of the at least one first detector element and the at least one second detector element comprises the following reactions:

$$glucose+O_2+H_2O \rightarrow gluconate+H_2O_2$$

$$H_2O_2 \rightarrow \tfrac{1}{2}O_2+H_2O$$

$$glucose+\tfrac{1}{2}O_2 \rightarrow gluconate.$$

12. The sensor apparatus of claim 1, wherein:
the first response characteristic and the second response characteristic are each further based at least in part on one or more features of the at least partly enclosed cavity being different for the at least one first detector element relative to the at least one second detector element;
a first base region of the at least partly enclosed cavity of the at least one first detector element is sized in at least a first area thereof so as to enable determination of the blood analyte concentration within a first specified range; and
a second base region of the at least partly enclosed cavity of the at least one second detector element is sized in at least a second area thereof so as to enable determination of the blood analyte concentration within a second specified range at least partially non-overlapping with the first specified range, the second area different from the first area.

13. The sensor apparatus of claim 1, wherein the enzymatic material comprises a material wherein the enzymes thereof are effectively immobilized, and the (i) immobilization of the enzymes, and (ii) the at least partial permeability of the non-enzymatic material of the non-enzymatic membrane to the analyte cooperate to allow the detection of the analyte concentration within a specified blood analyte concentration range for each of the at least one first detector element and the at least one second detector element while at least partly mitigating a foreign body response (FBR) by a tissue of a host living being within which the sensor apparatus is implanted.

14. The sensor apparatus of claim 6, wherein:
the at least one spout comprises a first aperture at an exterior surface thereof and a second aperture at an interior surface thereof, the second aperture in communication with the at least partly enclosed cavity;
the first shape comprises at least one first tapered interior surface extended between the first aperture and the second aperture of the at least one spout of the at least one first detector element; and
the second shape comprises at least one second tapered interior surface extended between the first aperture and the second aperture of the at least one spout of the at least one second detector element, the at least one second tapered interior surface having a different degree of tapering relative to the at least one first tapered interior surface.

15. The sensor apparatus of claim 14, wherein the at least one first tapered interior surface of the at least one spout of the at least one first detector element is configured to provide mechanical stability for the non-enzymatic membrane, the first aperture having a greater width than the second aperture.

16. The sensor apparatus of claim 1, wherein:
the at least one first detector element being configured to have the first response characteristic comprises the at least one first detector element being configured for determination of the blood analyte concentration within a first specified analyte concentration range; and
the at least one second detector element being configured to have the second response characteristic comprises the at least one second detector element being configured for determination of the blood analyte within a second specified analyte concentration range at least partially non-overlapping with the first specified analyte concentration range.

17. The analyte detection apparatus of claim 16, wherein:
a first fill-level of non-enzymatic material within the at least one spout of the first detector element is greater than a second fill-level of the non-enzymatic material within the at least one spout of the second detector element; and
the first specified analyte concentration range comprises a higher range relative to the second specified analyte concentration range.

18. The analyte detection apparatus of claim 16, wherein:
at least a first cross-sectional area of the at least one spout of the first detector element is less than a corresponding second cross-sectional area of the at least one spout of the second detector element; and
the first specified analyte concentration range comprises a higher range relative to the second specified analyte concentration range.

19. An analyte detection apparatus for use in a human being, comprising:
a substrate; and
a first detector element configured to detect blood analyte within a first analyte concentration response range, and a second detector element configured to detect blood analyte within a second analyte concentration response range at least partially non-overlapping with the first analyte concentration response range, each of the first detector element and the second detector element comprising:
one or more electrodes disposed on or within the substrate, each of the one or more electrodes comprising at least a terminal configured to enable electrical signals to be communicated from the respective ones of the one more electrodes to a circuit, the one or more electrodes comprising a working electrode, a counter electrode, and a reference electrode;

an electrolyte material in communication with at least a portion of each of the one or more electrodes;

a first membrane element in contact with at least a portion of the electrolyte material;

a second membrane element comprising (i) a cavity formed therein, the cavity having enzymatic material disposed therein, and (ii) at least one spout in communication with the cavity, the second membrane element disposed on an exterior surface of the analyte detection apparatus such that (i) the cavity is associated with the working electrode and is not associated with the counter electrode and the reference electrode, and (ii) the second membrane element forms a three-dimensional structure on the exterior surface of the analyte detection apparatus; and a non-enzymatic material configured to at least partly occlude at least a portion of the at least one spout and isolate tissue of the human being from the enzymatic material, yet permit analyte and oxygen therethrough, the enzymatic material configured to interact with at least a portion of the analyte and at least a portion of the oxygen entering the cavity via the at least one spout;

wherein the first analyte concentration response range and the second analyte concentration response range are each based at least on a combination of at least one size dimension of the cavity and a thickness of the enzymatic material disposed within the cavity being different for the first detector element relative to the second detector element.

20. The analyte detection apparatus of claim 19, wherein:
the substrate comprises a ceramic material, and the first membrane comprises a polymeric material;
the analyte comprises glucose, and the enzymatic material comprises glucose oxidase and catalase disposed in a crosslinked matrix;
the non-enzymatic material comprises cross-linked albumin; and
the second membrane comprises a silicone-based material.

21. The sensor apparatus of claim 19, wherein:
a first thickness of the enzymatic material for the first detector element is less than that of the second detector element; and
the first analyte concentration response range comprises a lower response range relative to the second analyte concentration response range.

22. A dynamically variable sensor apparatus, comprising:
signal processing circuitry; and
at least one first detector element and at least one second detector element each in signal communication with the signal processing circuitry, the at least one first detector element and the at least one second detector element each comprising:
an at least partly enclosed cavity, the at least partly enclosed cavity comprising at least one enzymatic substance, and at least one aperture in communication with the at least partly enclosed cavity, the aperture at least partly obscured with a non-enzyme, analyte-permeable substance;
an electrolyte layer; and
at least one electrode disposed at least partly within or contacting said electrolyte layer;
wherein said at least one first detector element and said at least one second detector element are each configured to utilize chemical interaction between at least the analyte and their respective enzymatic substance to enable generation of an electrical signal at their respective at least one electrode via their respective electrolyte layer, said electrical signal of the at least one first detector element and said electrical signal of the at least one second detector element each relating to a concentration of said analyte in a region external to their respective cavities;

wherein the at least one first detector element is configured to detect analyte within a first blood analyte concentration range, and the at least one second detector element is configured to detect analyte within a second blood analyte concentration range, the second blood analyte concentration range comprising a lower blood analyte concentration range relative to the first blood analyte concentration range, at least a lower threshold of the second blood analyte concentration range being less than a lower threshold of the first blood analyte concentration range, the first blood analyte concentration range and the second blood analyte concentration range each based on at least one of (i) a shape or dimension of the at least one aperture, (ii) a thickness of the non-enzyme yet permeable substance, or (iii) a shape or dimension of the cavity for the at least one first detector element being different from that for the at least one second detector element; and wherein the signal processing circuitry is configured for selective utilization of each of the electrical signal generated by the at least one first detector element and the electrical signal generated by the at least one second detector element while the sensor apparatus is operating within a living being, the selective utilization comprising:
identification of a blood analyte concentration;
determination of a trend of the identified blood analyte concentration as a function of at least time;
based at least in part on a determination that the blood analyte concentration is within the first blood analyte concentration range with the blood analyte concentration trending increasing, cause utilization of the electrical signal generated by the at least one first detector element;
based at least in part on a determination that the blood analyte concentration is within the first blood analyte concentration range with the blood analyte concentration trending decreasing, cause utilization of one or more of the electrical signal generated by the at least one first detector element or the electrical signal generated by the at least one second detector element;
based at least in part on a determination that the blood analyte concentration is within the second blood analyte concentration range with the blood analyte concentration trending increasing, cause utilization of one or more of the electrical signal generated by the at least one first detector element or the electrical signal generated by the at least one second detector element; and
based at least in part on a determination that the blood analyte concentration is within the second blood analyte concentration range with the blood analyte concentration trending decreasing, cause utilization of the electrical signal generated by the at least one second detector element.

23. A sensor apparatus, comprising:
signal processing circuitry; and
a first detector element configured to detect blood analyte within a first analyte concentration range, and a second detector element configured to detect blood analyte within a second analyte concentration range, the second analyte concentration range (i) at least partially non-overlapping with the first analyte concentration range and (ii) comprising a lower range relative to the first analyte concentration range, each of the first detector element and the second detector element in signal communication with the signal processing circuitry and comprising:
an electrolyte material;
a membrane element in communication with at least a portion of the electrolyte material, the membrane element comprising a cavity formed therein and at least one spout in communication with the cavity, the cavity having an enzymatic material disposed therein; and
a non-enzymatic material configured to at least partly occlude at least a portion of the at least one spout and isolate tissue of the human being from the enzymatic material, yet permit analyte therethrough, the enzymatic material disposed within the cavity and configured to interact with the analyte entering the cavity via the at least one spout;
at least one working electrode disposed on or within the substrate and in communication with the cavity via at least a portion of the electrolyte material, the at least one working electrode configured to utilize the interaction between the analyte and the enzymatic material to enable generation of an electrical signal;
wherein the signal processing circuitry is configured for selective utilization of each of the electrical signal generated by the at least one first detector element and the electrical signal generated by the at least one second detector element while the sensor apparatus is operating within a living being, the selective utilization comprising:
identification of each of (i) a blood analyte concentration, and (ii) a trend of the identified blood analyte concentration as a function of at least time;
based at least in part on a determination that the blood analyte concentration is within the first blood analyte concentration range with the blood analyte concentration exhibiting a first trend, cause selective utilization of one or both of the electrical signal generated by the at least one first detector element or the electrical signal generated by the at least one second detector element, the selective utilization based at least in part on the first trend; and
based at least in part on a determination that the blood analyte concentration is within the second blood analyte concentration range with the blood analyte concentration exhibiting a second trend, cause selective utilization of one or both of the electrical signal generated by the at least one first detector element or the electrical signal generated by the at least one second detector element, the selective utilization based at least in part on the second trend.

24. The sensor apparatus of claim 23, wherein the first detector element being configured to detect blood analyte within the first analyte concentration range and the second detector element being configured to detect blood analyte within the second analyte concentration range are each based at least on one or more of (i) at least one dimension of the at least one spout or (ii) a fill-level of the at least one spout with the non-enzymatic material being different for the first detector element relative to the second detector element.

25. The sensor apparatus of claim 24, wherein the at least one spout of the second detector element comprises one or more of (i) a greater cross-sectional area or (ii) a lower fill-level with the non-enzymatic material relative to the at least one spout of the first detector element.

26. A sensor apparatus, comprising:
a substrate;
signal processing circuitry;
logic in communication with the signal processing circuitry; and
a first detector element configured to detect blood analyte within a first analyte concentration range, and a second detector element configured to detect blood analyte within a second analyte concentration range, the second analyte concentration range (i) at least partially non-overlapping with the first analyte concentration range and (ii) comprising a lower range relative to the first blood analyte concentration range, each of the first detector element and the second detector element in communication with the signal processing circuitry and comprising:
an electrolyte material;
at least one working electrode disposed on or within the substrate and in communication with at least a portion of the electrolyte material, the at least one working electrode configured to utilize an interaction between blood analyte and an enzymatic material to enable generation of an electrical signal;
wherein the logic is configured to:
identify a trend of a blood analyte concentration as a function of at least time; and
cause selective utilization of one or both of the signal from the first detector element or the signal from the second detector element for use in determination of blood analyte level data based at least on the identified trend of the blood analyte concentration.

27. The sensor apparatus of claim 26, wherein the logic is further configured to identify a blood analyte concentration estimate, the cause of selective utilization of one or both of the signal from the first detector element or the signal from the second detector element further based on the identified blood analyte concentration estimate.

28. The sensor apparatus of claim 26, wherein each of the first detector element and the second detector element further comprises:
one or more non-working electrodes;
a membrane structure in communication with at least a portion of the electrolyte material, the membrane structure comprising (i) a cavity having the enzymatic material disposed therein and (ii) a spout in communication with the cavity, the membrane structure disposed on an exterior surface of the sensor apparatus such that the cavity is associated with the at least one working electrode and is not associated with the one or more non-working electrodes; and
a non-enzymatic membrane disposed within the spout, and configured to (i) at least partly occlude at least a portion of the spout and (ii) isolate tissue of the human being from the enzymatic material, yet permit analyte therethrough.

29. The sensor apparatus of claim 28, wherein the first detector element being configured to detect blood analyte within the first analyte concentration range and the second detector element being configured to detect blood analyte within the second analyte concentration range are each based at least on one or more of at least one dimension of the at least one spout or a fill-level of the at least one spout with the non-enzymatic material being different for the first detector element relative to the second detector element.

30. The sensor apparatus of claim 28, wherein the first detector element being configured to detect blood analyte within the first analyte concentration range and the second detector element being configured to detect blood analyte within the second analyte concentration range are each based at least on one or more of at least one dimension of the cavity or a thickness of the enzymatic material disposed within the cavity being different for the first detector element relative to the second detector element.

* * * * *